(12) United States Patent
Henkel et al.

(10) Patent No.: US 11,028,123 B2
(45) Date of Patent: Jun. 8, 2021

(54) CAPPING OF UNPROTECTED AMINO GROUPS DURING PEPTIDE SYNTHESIS

(71) Applicant: SANOFI-AVENTIS DEUTSCHLAND GMBH, Frankfurt am Main (DE)

(72) Inventors: Bernd Henkel, Frankfurt am Main (DE); Tobias Metzenthin, Frankfurt am Main (DE); Manfred Gerken, Frankfurt am Main (DE); Wolfgang Fiedler, Frankfurt am Main (DE)

(73) Assignee: SANOFI-AVENTIS DEUTSCHLAND GMBH, Frankfurt Am Main (DE)

( * ) Notice: Subject to any disclaimer, the term of this patent is extended or adjusted under 35 U.S.C. 154(b) by 0 days.

(21) Appl. No.: 16/380,321

(22) Filed: Apr. 10, 2019

(65) Prior Publication Data

US 2019/0330263 A1    Oct. 31, 2019

(30) Foreign Application Priority Data

Apr. 10, 2018 (EP) .................... 18166551

(51) Int. Cl.
    *C07K 1/04*      (2006.01)
    *C07K 1/10*      (2006.01)
    *C07K 1/06*      (2006.01)
    *C07K 14/605*    (2006.01)

(52) U.S. Cl.
    CPC .............. *C07K 1/10* (2013.01); *C07K 1/062* (2013.01); *C07K 1/064* (2013.01); *C07K 1/066* (2013.01); *C07K 14/605* (2013.01)

(58) Field of Classification Search
None
See application file for complete search history.

(56) References Cited

U.S. PATENT DOCUMENTS

| | | | |
|---|---|---|---|
| 5,424,286 A | 6/1995 | Eng | |
| 6,528,486 B1 | 3/2003 | Larsen | |
| 7,431,685 B2 | 10/2008 | Frey et al. | |
| 2005/0176079 A1 | 8/2005 | Chu | |
| 2008/0019911 A1 | 1/2008 | Xu et al. | |
| 2013/0289241 A1 | 10/2013 | Bai et al. | |
| 2015/0291682 A1 | 10/2015 | Vuilleumier et al. | |
| 2015/0322129 A1 | 11/2015 | Bossart | |
| 2017/0313740 A1 | 11/2017 | Wang et al. | |
| 2018/0155406 A1 | 6/2018 | Bossart et al. | |
| 2019/0330266 A1* | 10/2019 | Fiedler ................. | C07K 1/04 |

FOREIGN PATENT DOCUMENTS

| | | | |
|---|---|---|---|
| CN | 101357938 A | | 2/2009 |
| CN | 103819553 A | * | 5/2014 |
| CN | 103819553 A | | 5/2014 |
| CN | 104844706 | | 8/2015 |
| EP | 1076066 A1 | | 2/2001 |
| JP | H07-097401 | | 4/1995 |
| JP | 2011-510954 | | 4/2011 |
| WO | WO 98/05351 A1 | | 2/1998 |
| WO | WO 98/30231 A1 | | 7/1998 |
| WO | WO 99/07404 A1 | | 2/1999 |
| WO | WO 99/25727 A2 | | 5/1999 |
| WO | WO 99/25728 A1 | | 5/1999 |
| WO | WO 2000/12506 A2 | | 3/2000 |
| WO | WO 2000/12506 A3 | | 3/2000 |
| WO | WO 01/04156 A1 | | 1/2001 |
| WO | WO 2004/005342 A1 | | 1/2004 |
| WO | WO 2004/035623 A2 | | 4/2004 |
| WO | WO 2007/004675 | | 1/2007 |
| WO | WO 2006/134340 A9 | | 3/2009 |
| WO | WO 2011/012723 A1 | | 7/2009 |
| WO | WO 2010/011439 A2 | | 1/2010 |
| WO | WO 2010/148089 A1 | | 12/2010 |
| WO | WO 2011/160630 A2 | | 12/2011 |
| WO | WO 2012/088116 A2 | | 6/2012 |
| WO | WO 2013/192129 A1 | | 12/2013 |
| WO | WO 2013/192130 A1 | | 12/2013 |
| WO | WO 2014/049610 A2 | | 4/2014 |
| WO | WO 2014/056872 A1 | | 4/2014 |
| WO | WO 2014/096145 A1 | | 6/2014 |
| WO | WO 2015/067716 A1 | | 5/2015 |
| WO | WO 2015/086731 A1 | | 6/2015 |
| WO | WO 2015/086732 A1 | | 6/2015 |
| WO | WO 2015/086733 A1 | | 6/2015 |
| WO | WO 2015/155141 A1 | | 10/2015 |
| WO | WO 2016/198624 A1 | | 12/2016 |
| WO | WO 2017/162650 A1 | | 9/2017 |
| WO | WO 2018/069295 | | 4/2018 |

OTHER PUBLICATIONS

Machine translation of CN 103819553.*
Bhat et al., "A DPP-IV-resistant triple-acting agonist of GIP, GLP-1 and glucagon receptors with potent glucose-lowering and insulinotropic actions in high-fat-fed mice" Diabetologia. Jun. 2013;56(6):1417-24.
Bhat et al., "A novel GIP-oxyntomodulin hybrid peptide acting through GIP, glucagon and GLP-1 receptors exhibits weight reducing and anti-diabetic properties" Biochem Pharmacol. Jun. 1, 2013;85(11):1655-62.
Biancalana et al., "Molecular mechanism of Thioflavin-T binding to amyloid fibrils" Biochim Biophys Acta. Jul. 2010;1804(7):1405-12.
Druce et al., "Investigation of structure-activity relationships of Oxyntomodulin (Oxm) using Oxm analogs" Endocrinology. Apr. 2009;150(4):1712-22.

(Continued)

*Primary Examiner* — Fred H Reynolds
(74) *Attorney, Agent, or Firm* — Lathrop GPM LLP; James H. Velema, Esq.

(57) ABSTRACT

The present invention relates to a method for the synthesis of a polypeptide comprising a pre-determined amino acid sequence. The method according to the invention comprises coupling cycles of coupling an N-terminally protected amino acid building block C-terminally at an unprotected N-terminal amino group of an amino acid chain, wherein at least one coupling cycle comprises a coupling step (a), a capping step (b), and a de-protecting step (c).

21 Claims, 13 Drawing Sheets

Figure 1:
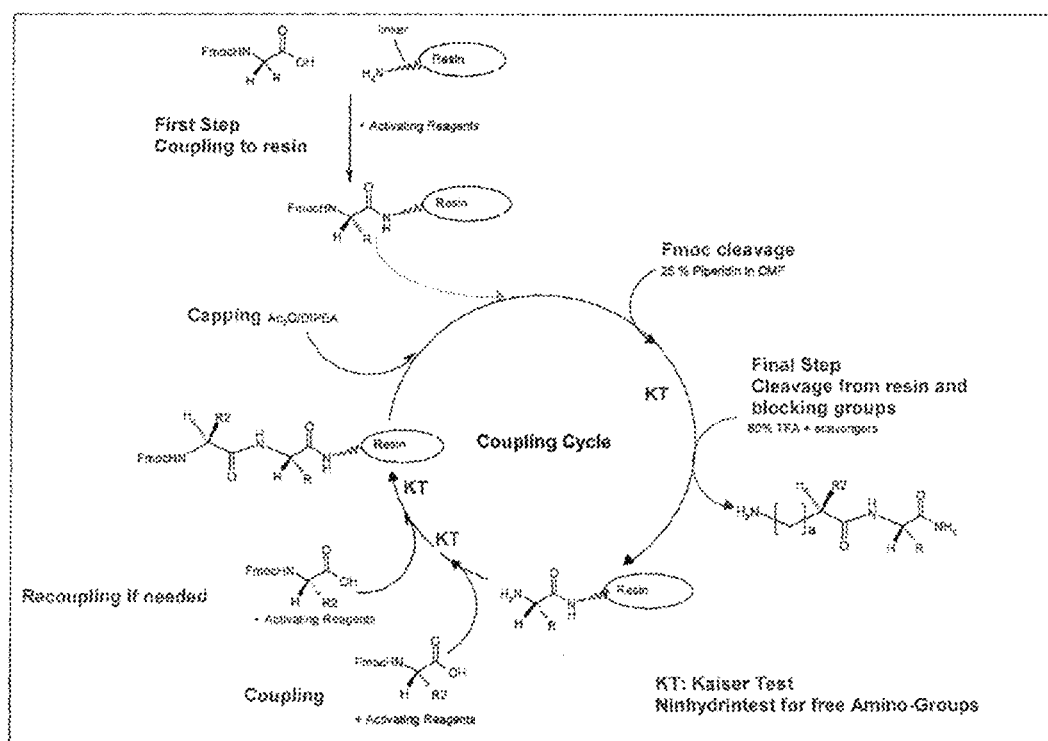

Specification includes a Sequence Listing.

(56) References Cited

OTHER PUBLICATIONS

Finan et al., "A rationally designed monomeric peptide triagonist corrects obesity and diabetes in rodents" Nat Med. Jan. 2015;21(1):27-36.
Hargrove et al., "Biological activity of AC3174, a peptide analog of exendin-4" Regul Pept. Jun. 7, 2007;141(1-3):113-9.
Heppner et al., "Glucagon regulation of energy metabolism" Physiol Behav. Jul. 14, 2010;100(5):545-8.
International Search Report for PCT/EP2017/081125, dated Feb. 3, 2018.
International Search Report for PCT/EP2017/081126, dated Feb. 3, 2018.
Kaiser et al., "Color test for detection of free terminal amino groups in the solid-phase synthesis of peptides" Anal Biochem. Apr. 1970;34(2):595-8.
Krstenansky et al., "Importance of the 10-13 region of glucagon for its receptor interactions and activation of adenylate cyclase" Biochemistry. Jul. 1, 1986;25(13):3833-9.
Naiki et al., "Fluorometric determination of amyloid fibrils in vitro using the fluorescent dye, thioflavin T1", Anal Biochem. Mar. 1989;177(2):244-9.
Pocai, "Action and therapeutic potential of oxyntomodulin", Mol Metab. Dec. 14, 2013;3(3):241-51.
Vojkovsky, "Detection of secondary amines on solid phase" Pept Res. Jul.-Aug. 1995;8(4):236-7.
Anonymous, "Introduction to Fmoc Solid Phase Peptide Synthesis", Jan. 1, 2006, SP055498187, Retrieved from the Internet: URL:https://cdn2.hubspot.net/hubfs/378579/1-PTI/Application%20Notes/904001902-Intro%20to20Fmoc%20SPPS-1.pdf?t=1498831943596.
European Search Report in related Application No. EP18166551.4, dated Aug. 16, 2018 (9 pages).
E. Atherton et al., Solid phase peptide synthesis, A Practical Approach, Oxford-IRL Press, New York, 1990, library catalog entry only.
E. Göke et al., "Exendin-4 Is a High Potency Agonist and Truncated Exendin-(9-39)-amide an Antagonist at the Glucagon-like Peptide 1-(7-36)-amide Receptor of Insulin-Secreting Beta Cells", Journal of Biological Chemistry, Sep. 15, 1993, vol. 268, No. 26, pp. 19650-19655.
G B Fields et al., "Solid-phase peptide synthesis and solid-state NMR spectroscopy of [Ala$^{3-15}$N][Val$^1$]gramicidin A", Proc. Natl. Acad. Sci. USA, Mar. 1988, vol. 85, No. 5, pp. 1384-1388.
G. Heinrich et al., "Pre-Proglucagon messenger ribonucleic acid: nucleotide and encoded amino acid sequences of the rat pancreatic complementary deoxyribonucleic acid", Endocrinology, 1984, vol. 115, No. 6, pp. 2176-2181.
H. Echner et al., "Eine neue Synthese von Thymosin $\alpha_1$", Liebigs Ann. Chem., Jul. 6, 1988, Issue 11, pp. 1095-1097.
International Search Report and Written Opinion for PCT International Patent Application No. PCT/EP2019/059083, dated Jun. 14, 2019.
International Search Report and Written Opinion for PCT International Patent Application No. PCT/EP2019/059090, dated May 2, 2019.
J. Eng et al., "Isolation and characterization of exendin-4, an exendin-3 analogue, from Heloderma suspectum venom", The Journal of Biological Chemistry, Apr. 15, 1992, vol. 267, No. 11, pp. 7402-7405.
J. Hoist, "Glucagon-like Peptide-1, a Gastrointestinal Hormone with a Pharmaceutical Potential", Current Medicinal Chemistry, 1999, vol. 6, No. 11, pp. 1005-1017, PMID:10519910.
J. Houben et al., Methods in Organic Chemistry, vol. E22a, Synthesis of Peptides and Peptidomimetics, M. Goodman, A. Felix, L. Moroder, C. Toniolo, (Eds.), Thieme Verlag, Stuttgart, New York, 2002, library catalog entry only.
J. Jones, The Chemical Synthesis of Peptides, New York, Oxford University Press, 1991, library catalog entry only.
J. Raufman, "Bioactive peptides from lizard venoms", Regulatory Peptides, 1996, vol. 61, pp. 1-18, PMID 8701022.
King et al., "A cleavage method which minimizes side reactions following Fmoc solid phase peptide synthesis", International Journal of Peptide & Protein Research, Sep. 1990, vol. 36, No. 3, pp. 255-266.
L. O. Uttenthal et al., "Molecular forms of glucagon-like peptide-1 in human pancreas and glucagonomas", Journal of Clinical Endocrinology and Metabolism, 1985, vol. 61, No. 3, pp. 472-479, PMID 2991321.
Liang et al. "Tumor-specific penetrating peptides-functionalized hyaluronic acid-d-α-tocopheryl succinate based nanoparticles for multi-task delivery to invasive cancers", Biomaterials 2015, vol. 71, pp. 11-23.
M. A. Nauck et al., "Glucagon-like peptide 1 (GLP-1) as a new therapeutic approach for type 2-diabetes", Exp. Clin. Endocrinol Diabetes, 1997, vol. 105 No. 4, pp. 187-195.
M. Lopez-Delgado et al., "Effects of glucagon-like peptide 1 on the kinetics of glycogen synthase α in hepatocytes from normal and diabetic rats", Endocrinology, 1998, vol. 139, No. 6, pp. 2811-2817, PMID 9285204.
M. Pennington et al., Peptide Synthesis Protocols, Humana Press, Totowa, New Jersey, 1995, library catalog entry only.
P. Sieber, "Modification of Tryptophan Residues During Acidolysis of 4-Methoxy-2, 3, 6-Trimethylbenzenesulfonyl Groups. Effects of Scavengers", Tetrahedron Letters, vol. 28, No. 15, 1987, pp. 1637-1640.
R. Eritja et al., "On the use of S-t-butylsulphenyl group for protection of cysteine in solid-phase peptide synthesis using FMOC-amino acids", Tetrahedron, 1987, vol. 43, No. 12, pp. 2675-2680.
Xiaoyu et al., "Recent Developments in the Research of Exendin-4 and Its Analogs", Progress in Pharmaceutical Sciences, 2007,vol. 31, No. 9, pp. 403-407, translation only.
Xu et al., "Recent Advances in Radionuclide-Labeled Analogues of Exendin-4 for Insulinoma Imaging", Cancer Res Prev Treat, 2013. vol. 42, No. 4, 20 pages, translation only.
Anonymous, "Introduction to Fmoc Solid Phase Peptide Systhesis", Protein Technologies, 2006, 6 pages.
International Preliminary Report on Patentability for PCT International Patent Application No. PCT/EP2019/059590, dated Mar. 20, 2020.
Cambridge Research Biomaterials, "Fmoc Solid-Phase Synthesis", 2020, obtained from url: https://www.crbdiscovery.com/technical/peptides/fmoc-solid-phase-synthesis/.
RAPP Polymere ("Rink Amide Linker on Aminomethyl Polystyrene Resin", Captured on Feb. 3, 2017).

\* cited by examiner

Figure 2

SEQ ID NO: 1 AVE0010 (44 AS)

H-G-E-G-T-F-T-S-D-L-S-K-Q-M-E-E-E-A-V-R-L-F-I-E-W-L-K-N-G-G-P-S-S-G-A-P-P-S-K-K-K-K-K-K-NH$_2$

SEQ ID NO: 2 Exendin-4 (39 AS)

H-G-E-G-T-F-T-S-D-L-S-K-Q-M-E-E-E-A-V-R-L-F-I-E-W-L-K-N-G-G-P-S-S-G-A-P-P-P-S-NH$_2$

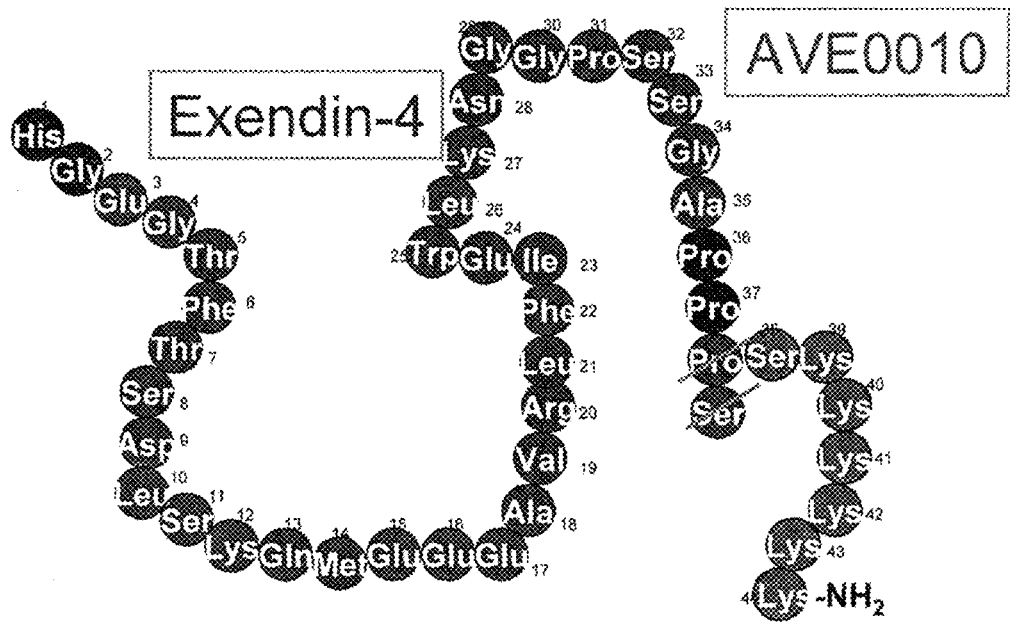

SEQ ID NO:3: Exendin-3 (J. Bio. Chem., 267, 1992, 7402-7405)

H-His-Ser-Asp-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$)

SEQ ID NO: 4: GLP-1 (7-36) amide

H-A-E-G-T-F-T-S-D-V-S-S-Y-L-E-G-Q-A-A-K-E-F-I-A-W-L-V-K-G-R- NH$_2$

Figure 6A
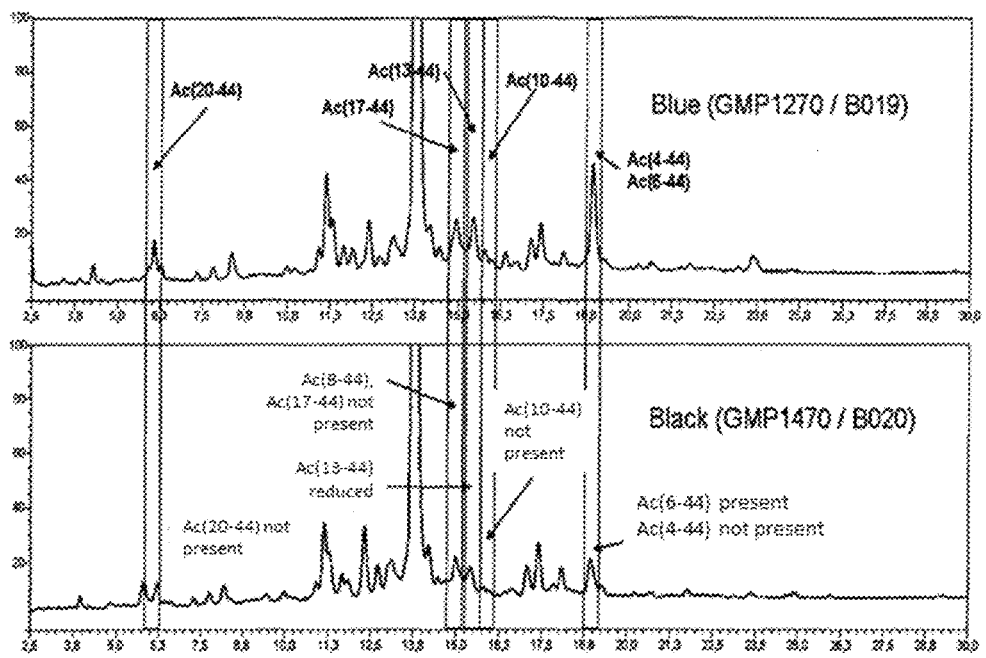
Figure 6B
Figure 6C
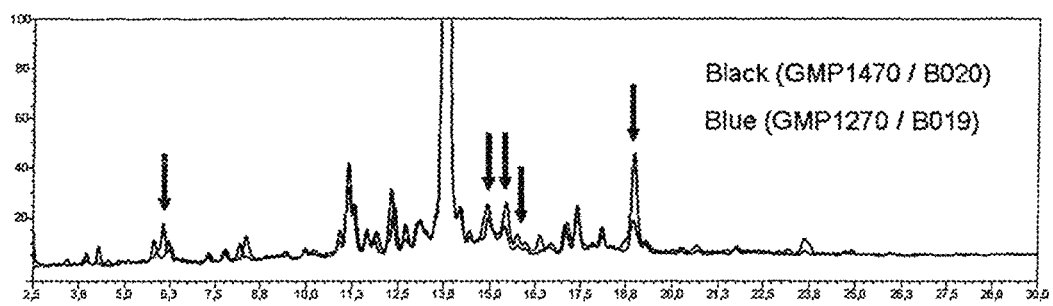

CAPPING OF UNPROTECTED AMINO GROUPS DURING PEPTIDE SYNTHESIS

RELATED APPLICATIONS

This application claims the benefit of European Patent Application No. 18166551.4, filed Apr. 10, 2018, the entire disclosure of which is hereby incorporated herein by reference in its entirety.

DESCRIPTION

The present invention relates to a method for the synthesis of a polypeptide comprising a pre-determined amino acid sequence. The method according to the invention comprises coupling cycles of coupling an N-terminally protected amino acid building block C-terminally at an unprotected N-terminal amino group of an amino acid chain, wherein at least one coupling cycle comprises a coupling step (a), a capping step (b), and a de-protecting step (c).

The invention further relates to a composition comprising 0.5-5% v/v of acetic anhydride and 0.2-2% v/v diisopropylethylamine, as well as its use as capping reagent for acetylation of an unprotected amino group in polypeptide synthesis.

Established methods of solid phase peptide synthesis teach coupling of the pre-determined C-terminal amino acid of the amino acid chain to be synthesized to a polymer carrier via a linker. The amino acid used for coupling is an amino acid building block having an N-terminally protected amino group, said protective group being a temporarily linked Fmoc group. After successful coupling, the Fmoc protective group is cleaved and the next Fmoc-protected amino acid building block is coupled with the free amino function of the previous amino acid building block. When the desired amino acid chain is synthesized, it is cleaved from the solid phase. FIG. 1 is giving an overview of the described approach.

As the coupling reaction is not always complete, the remaining free amino groups can be acetylated with acetic anhydride (see FIG. 1). This reaction is called capping. The aim of capping is preventing the occurrence of (N–1) impurities (i.e. products lacking an amino acid building block at one position), which are probably hard to separate from the desired end product.

In the literature, numerous capping mixtures for the solid phase synthesis of peptides are described. Fields et al. (PNAS 85, 1384-1388, 1988) uses acetic anhydride and diisopropylethylamine (DIPEA) in methylene chloride for the synthesis of gramicidine A. First, 1 equivalent of DIPEA in 20 ml methylene chloride is added. After five minutes, 4 equivalents of acetic anhydride are added. The total incubation time is 20 minutes. Eritja et al. (Tetrahetron 43, 2675-2680, 1987) teaches the use of approximately 9% of acetic anhydride and approximately 16% of DI PEA in DMF combined with an incubation time of 30 minutes for the capping process. Echner et al. discloses a mixture of acetic anhydride, pyridine and methylene chloride for the capping process (Liebigs Ann. Chem. 1988, 1095-1097).

The solid phase synthesis of lixisenatide (also known as AVE0010 or ZP-10) described in WO 01/04156 A1, which is enclosed herein by reference, comprises coupling of the individual Fmoc-protected amino acid building blocks in each the same way, without any capping reaction.

Lixisenatide has the sequence desPro$^{36}$exendin-4(1-39)-Lys$_6$-NH$_2$. This substance is disclosed in WO 01/04156, SEQ ID NO:93 (cf. SEQ ID NO:1 and FIG. 2 of the present application). Exendins are a group of peptides which can lower the blood glucose concentration. Exendins have a certain similarity to the sequence of GLP-1(7-36) (53%, Göke et al., J. Biol. Chem. 268, 19650-55). Exendin-3 and exendin-4 stimulate an increasing cellular cAMP production in pancreatic acinar cells of guinea pigs by interaction with the exendin receptors (Raufman, 1996, Reg. Peptides 61:1-18). In contrast to exendin-4, exendin-3 effects an increase of amylase release in pancreatic acinar cells. Exendins act as GLP-1 antagonists.

Glucagon-like peptide 1 (GLP-1) is an endocrine hormone which enhances the insulin response after oral uptake of glucose or fat. GLP-1 generally lowers the glucagon concentrations, slows down gastric emptying, stimulates the (pro-) insulin biosynthesis, increases the sensibility to insulin and stimulates the insulin-independent glycogen biosynthesis (Hoist (1999), Curr. Med. Chem. 6:1005, Nauck et al. (1997), Exp. Clin. Endocrinol. Diabetes 105:187, Lopez-Delgado et al. (1998), Endocrinology 139:2811). Human GLP-1 has 37 amino acid residues (Heinrich et al., Endocrinol. 115:2176 (1984), Uttenthal et al., J. Clin. Endocrinol. Metabol. (1985), 61:472). Active fragments of GLP-1 include GLP-1(7-36) and GLP-1(7-37).

It was suggested that exendin-3, exendin-4 and exendin agonists can be used for the treatment of diabetes mellitus and the prevention of hyperglycemia, as they reduce gastric emptying and motility (U.S. Pat. No. 5,424,286 and WO 98/0535 A1).

Exendin analogues may be characterized by amino acid substitutions and/or C-terminal truncations of the native exendin-4 sequence. Such exendin analogues are described in WO 99/07404, WO 99/25727 and WO 99/25728.

The inventors have found that the crude product of a common solid phase synthesis of lixisenatide with Fmoc-protected amino acid building blocks exhibits certain acetylated erroneous sequences in increased amounts with regard to other acetylated erroneous sequences. These unexpectedly pronounced impurities are in particular Ac(20-44)(SEQ ID NO:20), Ac(17-44)(SEQ ID NO:17), Ac(13-44)(SEQ ID NO:15), Ac(10-44)(SEQ ID NO:12) and Ac(4-44)(SEQ ID NO:6).

The problem to be solved by the present invention is to reduce the amount of acetylated erroneous sequences occurring in peptide synthesis and therefore, to enhance the yield of the peptide synthesis. In particular, the amount of those acetylated erroneous sequences having an increased amount in the crude product should be reduced.

It has been found that during the capping step of lixisenatide solid phase synthesis, the Fmoc-protective group is undesirably cleaved from some of the amino acid building blocks just coupled. This undesirable cleavage was only detected for capping at certain amino acid positions during the synthesis cycle. Five of these positions are:
- capping after coupling of Arg(20),
- capping after coupling of Glu(17),
- capping after coupling of Gln(13),
- capping after coupling of Leu(10),
- capping after coupling of Gly(4).

A further problem to be solved by the present application is thus, to provide capping conditions under which the undesired acetylated products are no longer present in such increased amounts.

Surprisingly, it was found that applying milder capping conditions leads to lower by-product concentrations in the crude product or even their complete eradication. By reducing or completely eliminating the by-products Ac(17-44) (SEQ ID NO:17), Ac(13-44)(SEQ ID NO:15), and Ac(10-

44)(SEQ ID NO:12), whose chromatographic peaks are close to that of the intended product, the purification of the intended product from the crude product is strongly facilitated. As less mixed fractions occur, the yield of purified lixisenatide increases. The yield further increases as the concentration of by-products Ac(20-44)(SEQ ID NO:20) and Ac(4-44)(SEQ ID NO:6), the peaks of which are further away from the intended product peak, are also minimized by the mild capping conditions.

One aspect of the present invention relates to a method for the synthesis of a polypeptide comprising a pre-determined amino acid sequence, the method comprising coupling cycles of amino acid building blocks to an amino acid chain, wherein said amino acid building blocks comprise an unprotected C-terminal carboxyl group and a protected N-terminal amino group, and wherein said amino acid chain comprises an unprotected N-terminal amino group, wherein at least one coupling cycle comprises the steps:

(a) coupling the amino acid building block C-terminally at the unprotected N-terminal amino group of the amino acid chain, so that an amide bond is formed between the amino acid chain and the amino acid building block, (b) contacting the product obtained in step (a) with a capping reagent comprising a capping compound, wherein the capping compound binds to an unprotected N-terminal amino group of the amino acid chain to which no building block has been coupled in step (a), and (c) de-protecting the N-terminal amino group of the amino acid building block.

In the present invention, "capping reagent", "capping composition" or "capping mixture" are used interchangeably. The reagent may be prepared before step (b), or the components of the capping reagent are added during step (b).

An amino acid chain, capped in step (b), is not capable of coupling a further amino acid building block, so that chain elongation of this molecule is terminated.

During the synthesis of the polypeptide, coupling cycles of amino acid building blocks are performed such that the amino acid chain of the polypeptide is formed building block per building block. For the coupling step, state-of-the-art techniques can be used, in particular a solid phase synthesis on the basis of Fmoc-protected amino acid building blocks. All kinds of solid phases suitable for the solid phase synthesis of peptides can be used. In particular, a solid phase comprising a resin can be used. The resin can be a Rink resin (Rink amide resin) or a Tentagel® resin. In a preferred aspect, the solid phase resin is a Rink resin or Rink amide resin.

Cycles comprising the steps (a), (b) and (c) according to the invention can be repeated once or several times. For each amino acid building block to be coupled one cycle is performed. The respective amino acid building block is independently selected for each cycle dependent on the pre-determined amino acid sequence. All kinds of amino acid building blocks, as described herein, can be used.

The method according to the invention can combine coupling cycles which are the same or different in relation to the capping step conditions, such as the capping temperature, the capping reagent composition or/and the capping duration. In one aspect all coupling cycles according to the invention are performed under the same capping conditions. In another aspect at least one capping step differs from the other capping steps according to the invention, e.g. by a modified capping temperature, the capping reagent composition or/and the capping duration. In one aspect, the method according to the invention comprises more than one capping step condition, e.g. two, three, four or five different capping step conditions over the whole polypeptide synthesis.

In one aspect, the method according to the invention comprises at least one coupling cycle, at least two coupling cycles, at least three coupling cycles, at least four coupling cycles, or at least five coupling cycles comprising a capping step (b).

The capping compound is preferably selected from the group consisting of acetic anhydride (CAS 108-24-7), homologues of acetic anhydride, benzoyl chloride (CAS 98-88-4), N-(benzyloxycarbonyloxy)succinimide (CAS 13139-17-8), benzyl chloroformate (CAS 501-53-1), esters of chloroformic acid, 1-acetylimidazole (CAS 2466-76-4), di-tert-butyl dicarbonate (CAS 24424-99-5) and N-(tert-butoxycarbonyloxy)succinimide (CAS 13139-12-3). In a preferred aspect, the capping compound is selected from acetic anhydride and homologues of acetic anhydride and is preferably acetic anhydride.

In one aspect, the capping reagent comprises acetic anhydride in a concentration of 0.5-5% v/v. In a preferred aspect the concentration of acetic anhydride is 1-3% v/v, more preferred 2% v/v.

In another aspect, the capping reagent comprises homologues of acetic anhydride in a concentration of 0.5-5% v/v. In a preferred aspect the concentration of the homologues of acetic anhydride is 1-3% v/v, more preferred 2% v/v.

In another aspect, the capping reagent comprises benzoyl chloride in a concentration of 0.5-5% v/v. In a preferred aspect the concentration of benzoyl chloride is 1-3% v/v, more preferred 2% v/v.

In another aspect, the capping reagent comprises N-(benzyloxycarbonyloxy)succinimide in a concentration of 0.5-5% v/v. In a preferred aspect the concentration of N-(benzyloxycarbonyloxy)succinimide is 1-3% v/v, more preferred 2% v/v.

In another aspect, the capping reagent comprises benzyl chloroformate in a concentration of 0.5-5% v/v. In a preferred aspect the concentration of benzyl chloroformate is 1-3% v/v, more preferred 2% v/v.

In another aspect, the capping reagent comprises esters of chloroformic acid, in a concentration of 0.5-5% v/v. In a preferred aspect the concentration of the esters of chloroformic acid is 1-3% v/v, more preferred 2% v/v.

In another aspect, the capping reagent comprises 1-acetylimidazole, in a concentration of 0.5-5% v/v. In a preferred aspect the concentration of 1-acetylimidazole is 1-3% v/v, more preferred 2% v/v.

In another aspect, the capping reagent comprises esters of di-tert-butyl dicarbonate, in a concentration of 0.5-5% v/v. In a preferred aspect the concentration of di-tert-butyl dicarbonate is 1-3% v/v, more preferred 2% v/v.

In another aspect, the capping reagent comprises esters of N-(tert-butoxycarbonyloxy)succinimide in a concentration of 0.5-5% v/v. In a preferred aspect the concentration of N-(tert-butoxycarbonyloxy)succinimide is 1-3% v/v, more preferred 2% v/v.

The capping reagent can comprise diisopropylethylamine (also termed DIPEA, N-ethyldiisopropylamine or N,N-diisopropylethylamine). In one aspect, the capping reagent comprises diisopropylethylamine, wherein the concentration of diisopropylethylamine can be 0.2-2% v/v and preferably is 0.5-2% v/v. A preferred concentration of diisopropylethylamine is 1% v/v.

In one aspect, the capping reagent comprises diisopropylethylamine and acetic anhydride, wherein the concentration of diisopropylethylamine can be 0.2-2% v/v and preferably is 0.5-2% v/v, and the concentration of acetic anhydride can be 0.5-5% v/v and preferably is 1-3% v/v.

In one aspect, the capping composition or capping reagent comprises diisopropylethylamine in a concentration of about 1% v/v, and acetic anhydride in a concentration of about 2% v/v.

In the method of the invention, the N-terminal amino group of the amino acid building block preferably is a base-labile protecting group, more preferably Fmoc.

The solvent used in the capping step is preferably a polar non-aqueous solvent, such as acetonitrile, dimethyl sulfoxide (DMSO), methanol, methylene chloride, N,N-dimethylacetamide (DMA), N,N-dimethylformamide (DMF), N-methylpyrrolidone, or mixtures thereof. In a preferred aspect, the solvent used in the capping step is DMF.

In the present invention, the term "about" or "approximately" means a range of ±10%, ±5% or ±1%.

The capping reaction (b) according to the invention can be performed at room temperature. Room temperature according to the invention is related to a temperature between about 15-25° C., a temperature ranging from about 20-23° C., a temperature ranging from about 19-21° C. or a temperature of about 20° C.

In the method of the invention, step (b) preferably is performed for 5 to 15 min, preferably for 10 min.

In a preferred aspect, step (b) is performed for 10 min with a capping reagent comprising 2% v/v acetic anhydride and 1% v/v DIPEA.

In another preferred aspect, step (b) is performed for 10 min with a capping reagent comprising 2% v/v acetic anhydride and 1% v/v DIPEA in DMF at positions Arg(20), Glu(17), Gln(13), Leu(10) or/and Gly(4) of the lixisenatide or exendin-4 sequence.

In yet another preferred aspect, step (b) is performed for 10 min with a capping reagent comprising 2% v/v acetic anhydride and 1% v/v DIPEA in DMF at positions Arg(20), Glu(17), Gln(13), Leu(10) and Gly(4) of the lixisenatide or exendin-4 sequence at room temperature, as described herein.

In one aspect, the method according to the invention can comprise at least one coupling cycle, at least two coupling cycles, at least three coupling cycles, at least four coupling cycles or at least five coupling cycles without a capping step, in particular at positions different from Arg(20), Glu(17), Gln(13), Leu(10) or/and Gly(4) of the lixisenatide or exendin-4 sequence.

In another aspect, the method according to the invention comprises capping according to step (b) after coupling of the amino acid building block Arg(20), Glu (17), Gln(13), Leu(10) or/and Gly(4) of the lixisenatide or exendin-4 sequence, in particular for about 10 min with a capping reagent comprising 2% v/v acetic anhydride and 1% v/v diisopropylethylamine. Step (b) can be performed after coupling of an Arg, Glu, Gln, Leu or/and Gly residue in step (a), in particular Arg(20), Glu (17), Gln(13), Leu(10) or/and Gly(4) of the lixisenatide or exendin-4 sequence. Preferably, in other amino acid positions, no capping step is performed, or/and capping is performed for 20 min with 10% acetic anhydride and 5% v/v DIPEA in DMF. In particular, capping is performed at room temperature, as described herein.

In yet another aspect of the invention the method according to the invention comprises capping according to step (b) after coupling of all amino acid building blocks of the lixisenatide or exendin-4 sequence, in particular for about 10 min with a capping reagent comprising 2% v/v acetic anhydride and 1% v/v diisopropylethylamine. Step (b) can be performed after coupling of all amino acid residues of the lixisenatide or exendin-4 sequence in step (a). In single amino acid coupling steps, capping can be omitted. Step (b) can be performed after coupling of at least 30 or at least 35 amino acid residues of the lixisenatide or exendin-4 sequence in step (a).

In one aspect, the method according to the invention can comprise at least one coupling cycle without a capping step (b) and at least one coupling cycle comprising a capping step (b) as described herein. In one aspect, the method according to the invention can comprise at least one coupling cycle, at least two coupling cycles, at least three coupling cycles, at least four coupling cycles, or at least five coupling cycles without a capping step (b) and at least one coupling cycle, at least two coupling cycles, at least three coupling cycles, at least four coupling cycles, or at least five coupling cycles comprising a capping step (b) as described herein. No capping is performed in particular at positions different from Arg(20), Glu(17), Gln(13), Leu(10) or/and Gly(4) of the lixisenatide or exendin-4 sequence.

In one aspect, the method according to the invention can comprise at least one coupling cycle, at least two coupling cycles, at least three coupling cycles, at least four coupling cycles, or at least five coupling cycles comprising the steps (a), (b') and (c), wherein capping step (b') is performed under different conditions as capping step (b). A coupling cycle comprising step (b') is particularly applied for coupling of an amino acid building block, different from Arg(20), Glu(17), Gln(13), Leu(10) or/and Gly(4) of the lixisenatide or exendin-4 sequence. In one aspect, step (b') can use a capping reagent comprising about 10% v/v acetic anhydride and about 5% v/v diisopropylethylamine in DMF, e.g. performed for about 20 min.

In one aspect, the method according to the invention can comprise at least one coupling cycle comprising a capping step (b) according to the invention and at least one coupling cycle comprising a capping step (b') as described herein. In one aspect, the method according to the invention can comprise at least one coupling cycle, at least two coupling cycles, at least three coupling cycles, at least four coupling cycles, or at least five coupling cycles comprising a capping step (b) according to the invention and at least one coupling cycle, at least two coupling cycles, at least three coupling cycles, at least four coupling cycles, or at least five coupling cycles comprising a capping step (b') as described herein.

For coupling of an amino acid building block as described herein, comprising coupling of more than one amino acid in one single cycle, a coupling cycle comprising step (b') is preferably used, e.g. for the coupling of dipeptides such as Pro-Pro or His-Gly by using the amino acid building blocks Fmoc-Pro-Pro-OH and Fmoc-His(Trt)-Gly-OH, respectively.

Methods for the performance of a coupling step according to step (a) and a de-protecting step according to step (c) are known by the person skilled in the art. The peptide synthesis is preferably performed in the form of a solid phase synthesis. In a preferred aspect, the coupling cycles are performed from the C-terminus to the N-terminus of the sequence to be synthesized. Reaction conditions for steps (a) and (c) applied in a solid phase peptide synthesis from the C-terminus to the N-terminus by amino acid building blocks are known by the person skilled in the art.

An amino acid building block according to the invention is a compound which is prolonging the amino acid chain to be synthesized by one or more amino acids in one cycle of the peptide synthesis. In a preferred aspect, an amino acid building block according to the invention prolongs the amino acid chain to be synthesized by 1, 2, 3, or 4 amino acids. In a particularly preferred aspect, the amino acid building block according to the invention prolongs the amino acid chain to be synthesized by one or two amino acids.

The amino acid building block according to the invention preferably comprises one amino acid (mono amino acid building block) or an oligopeptide comprising 2, 3, 4 or more amino acids. In a preferred aspect, the amino acid building block according to the invention comprises one amino acid or a peptide, comprising two amino acids such as e.g. Pro-Pro or His-Gly. Amino acids of an amino acid building block comprising more than one amino acid are preferably linked by peptide bonds. Particularly preferred amino acid building blocks comprising two amino acids are Fmoc-Pro-Pro-OH and Fmoc-His(Trt)-Gly-OH.

It was found that using Fmoc-His(Trt)-Gly-OH instead of amino acid building blocks for His and Gly at positions 1 and 2 in the synthesis of lixisenatide and exendin-4 enables the prevention of undesired DesGly(2)-lixisenatide. Moreover, the obtained lixisenatide did not show enhanced values of D-His resulting from racemization.

Fmoc-His(Trt)-Gly-OH can e.g. be formed by a method comprising the steps of:
i) reacting Fmoc-His(Trt)-OH and H-Gly-OBzl tosylate, and
ii) cleaving the benzyl group of the product obtained in step i) to obtain Fmoc-His(Trt)-Gly-OH.

Exemplary reaction conditions are set forth in example 3.

The amino acid building blocks according to the invention can comprise suitable modifications in order to selectively prolong the amino acid chain at the desired positions only. Modifications of the amino acid building block can be performed at the N-terminus, at the C-terminus or/and at the side chains of the amino acids.

To protect the N-terminal amino function of the amino acid building block (i.e. the amino group which is, after successful coupling, the N-terminus of the amino chain), all kinds of protective groups commonly used for the synthesis of peptides, especially for the solid phase synthesis of polypeptides, can be used. The person skilled in the art knows those kinds of suitable temporary protective groups. In a preferred aspect, protective groups which are unstable in alkaline environment can be used. In a preferred aspect the N-terminal amino group of the amino acid building block is protected by an Fmoc protective group.

The C-terminal carboxy group of the amino acid building block preferably remains unprotected.

The amino acid building block according to the invention can comprise, independently from one another, D-amino acids and glycine, L-amino acids and glycine or/and combinations thereof. In a preferred aspect the amino acids of the amino acid building block according to the invention are selected independently from one another from L-amino acids and glycine. In a preferred aspect, the amino acids can be selected from α-amino acids. In a further aspect the amino acids can be selected from naturally occurring amino acids such as amino acids naturally occurring in polypeptides. In another aspect the amino acid building block according to the invention can comprise artificial amino acids such as Met(O) (methionine sulfoxide or methionine sulfone), Trp(O$_2$) (N-formylkynurenine) or/and isoAsp (β-aspartate or isoaspartate). In a still further preferred aspect the amino acids are selected from Ser, Thr, Trp, Lys, Ala, Asn, Asp, Val, Met, Phe, Ile, Pro, Arg, Glu, Gln, Leu, in particular each in the D-form or each in the L-form, and Gly. In a particularly preferred aspect the amino acid building block according to the invention comprises amino acids selected from Arg, Glu, Gln, Leu, in particular each in the D-form or each in the L-form, and Gly.

In particular the amino acids are selected independently from each other, for example independently from Ser, Thr, Trp, Lys, Ala, Asn, Asp, Val, Met, Phe, Ile, Pro, Arg, Glu, Gln, Leu, in particular each in the D-form or each in the L-form, and Gly.

In one aspect, at least one side chain of the amino acid building block according to the invention can be protected by a further protective group. The further protective group is preferably orthogonal to the N-terminal protective group. Suitable protective groups for said side chains are known by the person skilled in the art. Examples for suitable protective groups are e.g. Trt, Boc, Bzl, Pdf, tBu and OtBu, which can be used for the protection of specific side chains. The person skilled in the art is aware of which side chain needs to be protected by which kind of protective group. In one aspect, amino acid building blocks as mentioned in Example 1.4 can be used. In case the amino acid building block comprises more than one side chain, one or more of these side chains can be protected by protective groups, independently selected from suitable protective groups as known by the person skilled in the art.

The polypeptide to be synthesized may be each possible peptide with a pre-determined sequence. In a preferred aspect, the polypeptide to be synthesized is a GLP-1 agonist. The polypeptide can be a GLP-1 agonist, wherein the GLP-1 agonist is selected from the group consisting of GLP-1 and analogues and derivatives thereof, exendin-3 and analogues and derivatives thereof, exendin-4 and analogues and derivatives thereof. In a preferred aspect the polypeptide is selected from the group consisting of exendin-4 and lixisenatide. Lixisenatide is most preferred. In a further preferred aspect the polypeptide is selected from albiglutide, dulaglutide and semaglutide.

Exendin-3, analogues and derivatives of exendin-3, exendin-4 and analogues and derivatives of exendin-4 are described in WO 01/04156, WO 98/30231, U.S. Pat. No. 5,424,286, EP 99610043.4 and WO 2004/005342. These documents are incorporated herein by reference. Exendin-3, exendin-4 and the analogues and derivatives thereof described in these documents can be synthesized by the method according to the invention, whereas additional modifications can be performed after completion of the synthesis.

Lixisenatide (SEQ ID NO:1, FIG. 2), exendin-4 (SEQ ID NO:2, FIG. 2) and exendin-3 (SEQ ID NO:3, FIG. 2) have a high degree of sequence identity. Sequences of lixisenatide and exendin-4 are identical at positions 1-37. Sequence 1-39 of exendin-4 is identical to exendin-3 at 37 of 39 positions (94%) (J. Biol. Chem. 267, 1992, 7402-7405). Sequence positions are given herein with respect to the sequence of lixisenatide or exendin-4. Starting from these sequences, the person skilled in the art can readily determine corresponding positions in other sequences.

Analogues and derivatives of exendin-3 or/and exendin-4 particularly comprise a modified amino acid sequence. In one aspect, the amino acid sequence is modified by deletion of one or more amino acids (e.g. desPro$^{36}$, desPro$^{37}$, desAsp$^{28}$, desMet(O$^{14}$) in exendin-4 and the respective positions in exendin-3). In one aspect, one or more amino acids can be replaced (e.g. Met(O$^{14}$), Trp(O$_2$)$^{25}$, isoAsp$^{28}$, Asp$^{28}$, Pro$^{38}$ in exendin-4 and the respective positions in exendin-3), wherein naturally occurring or artificial amino acids such as e.g. Met(O) (methionine sulfoxide or methionine sulfone), Trp(O$_2$) (N-formylkynurenine) or/and isoAsp (β-aspartate or isoaspartate) can be introduced. Artificial amino acids can readily be introduced in the sequence by using the respective amino acid building blocks in the synthesis cycle.

In one aspect the C-terminus or/and the N-terminus of the polypeptide can be modified, e.g. by the addition of sequences such as -(Lys)-, -(Lys)$_2$-, -(Lys)$_3$-, -(Lys)$_4$-, -(Lys)$_5$-, -(Lys)$_6$-, and -Asn-(Glu)$_5$-. In a preferred aspect, additional amino acid sequences are e.g. -(Lys)$_4$-, -(Lys)$_5$-, -(Lys)$_6$- and -Asn-(Glu)$_5$-. The C-terminal carboxy group is preferably an acid amine group (—NH$_2$). Optionally, the modification of the C-terminus or/and the N-terminus is performed in a separate step after completion of the synthesis cycles of the method according to the invention.

After completion of the synthesis cycles of the method according to the invention, pharmaceutically acceptable salts of the synthesized polypeptides can optionally be formed in an additional step. Methods for the formation of pharmaceutically acceptable salts of polypeptides are known by the person skilled in the art. Preferred pharmaceutically acceptable salts are e.g. acetate salts.

In one aspect, the GLP-1 agonist is preferably selected from the group consisting of exendin-4, analogues and derivatives thereof and pharmaceutically acceptable salts thereof.

A further preferred GLP-1 agonist is an analogue of exendin-4 selected from the group consisting of:
H-desPro$^{36}$-exendin-4-Lys$_6$-NH$_2$,
H-des(Pro$^{36,37}$)-exendin-4-Lys$_4$-NH$_2$,
H-des(Pro$^{36,37}$)-exendin-4-Lys$_5$-NH$_2$, and pharmaceutically acceptable salts thereof.

A further preferred GLP-1 agonist is an analogue of exendin-4 selected from the group consisting of
desPro$^{36}$[Asp$^{28}$]exendin-4 (1-39),
desPro$^{36}$[IsoAsp$^{28}$]exendin-4 (1-39),
desPro$^{36}$[Met(O)$^{14}$,Asp$^{28}$]exendin-4 (1-39),
desPro$^{36}$[Met(O)$^{14}$,IsoAsp$^{28}$]exendin-4 (1-39),
desPro$^{36}$[Trp(O$_2$)$^{25}$,Asp$^{28}$]exendin-2 (1-39),
desPro$^{36}$[Trp(O$_2$)$^{26}$,IsoAsp$^{26}$]exendin-2 (1-39),
desPro$^{36}$[Met(O)$^{14}$Trp(O$_2$)$^{25}$,Asp$^{28}$]exendin-4 (1-39),
desPro$^{36}$[Met(O)$^{14}$Trp(O$_2$)$^{25}$,IsoAsp$^{28}$]exendin-4 (1-39),
and pharmaceutically acceptable salts thereof.

A further preferred GLP-1 agonist is an analogue of exendin-4 selected from the groups as described above, further modified with a -Lys$_6$-NH$_2$ peptide at the C-terminus.

A further preferred GLP-1 agonist is an analogue of exendin-4 selected from the group consisting of:
H-(Lys)$_6$-desPro$^{36}$[Asp$^{28}$]exendin-4(1-39)-Lys$_6$-NH$_2$,
desAsp$^{28}$Pro$^{36}$,Pro$^{37}$,Pro$^{38}$exendin-4(1-39)-NH$_2$,
H-(Lys)$_6$-desPro$^{36}$,Pro$^{37}$,Pro$^{38}$[Asp$^{28}$]exendin-4(1-39)-NH$_2$,
H-Asn-(Glu)$_5$desPro$^{36}$,Pro$^{37}$,Pro$^{38}$[Asp$^{28}$]exendin-4(1-39)-NH$_2$,
desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$,Pro$^{37}$,Pro$^{38}$[Asp$^{28}$]exendin-4(1-39)-(Lys)$_6$-NH$_2$,
H-Asn-(Glu)$_5$-desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$[Trp(O$_2$)$^{25}$,Asp$^{28}$]exendin-4(1-39)-Lys$_6$-NH$_2$,
H-desAsp$^{28}$ Pro$^{36}$,Pro$^{37}$,Pro$^{38}$[Trp(O$_2$)$^{25}$]exendin-4(1-39)-NH$_2$,
H-(Lys)$_6$-desPro$^{36}$,Pro$^{37}$,Pro$^{38}$[Trp(O$_2$)$^{25}$,Asp$^{28}$]exendin-4(1-39)-NH$_2$,
H-Asn-(Glu)$_5$-desPro$^{36}$,Pro$^{37}$,Pro$^{38}$[Trp(O$_2$)$^{25}$,Asp$^{28}$]exendin-4(1-39)-NH$_2$,
desPro$^{36}$,Pro$^{37}$,Pro$^{38}$[Trp(O$_2$)$^{25}$,Asp$^{28}$]exendin-4(1-39)-(Lys)$_6$-NH$_2$,
H-(Lys)$_6$-desPro$^{36}$,Pro$^{37}$,Pro$^{38}$[Trp(O$_2$)$^{25}$,Asp$^{28}$]exendin-4(1-39)-(Lys)$_6$-NH$_2$,
H-Asn-(Glu)$_5$-desPro$^{36}$,Pro$^{37}$,Pro$^{38}$[Trp(O$_2$)$^{25}$,Asp$^{28}$]exendin-4(1-39)-(Lys)$_6$-NH$_2$,
H-(Lys)$_6$-desPro$^{36}$[Met(O)$^{14}$,Asp$^{28}$]exendin-4(1-39)-Lys$_6$-NH$_2$,
desMet(O)$^{14}$ Asp$^{28}$ Pro$^{36}$, Pro$^{37}$, Pro$^{38}$exendin-4(1-39)-NH$_2$,
H-(Lys)$_6$-desPro$^{36}$,Pro$^{37}$,Pro$^{38}$[Met(O)$^{14}$,Asp$^{28}$]exendin-4(1-39)-NH$_2$,
H-Asn-(Glu)$_5$-desPro$^{36}$,Pro$^{37}$,Pro$^{38}$[Met(O)$^{14}$,Asp$^{28}$]exendin-4(1-39)-NH$_2$,
desPro$^{36}$,Pro$^{37}$,Pro$^{38}$[Met(O)$^{14}$,Asp$^{28}$]exendin-4(1-39)-(Lys)$_6$-NH$_2$,
H-(Lys)$_6$-desPro$^{36}$,Pro$^{37}$,Pro$^{38}$[Met(O)$^{14}$,Asp$^{28}$]exendin-4(1-39)-Lys$_6$-NH$_2$,
H-Asn-(Glu)$_5$-desPro$^{36}$,Pro$^{37}$,Pro$^{38}$[Met(O)$^{14}$,Asp$^{28}$] exendin-4(1-39)-(Lys)$_6$-NH$_2$,
H-(Lys)$_6$-desPro$^{36}$[Met(O)$^{14}$, Trp(O$_2$)$^{25}$,Asp$^{28}$]exendin-4(1-39)-Lys$_6$-NH$_2$,
desAsp$^{28}$Pro$^{36}$, Pro$^{37}$, Pro$^{38}$[Met(O)$^{14}$, Trp(O$_2$)$^{25}$,Asp$^{28}$]exendin-4(1-39)-NH$_2$,
H-(Lys)$_6$-desPro$^{36}$, Pro$^{37}$, Pro$^{38}$[Met(O)$^{14}$, Trp(O$_2$)$^{25}$, Asp$^{28}$]exendin-4(1-39)-NH$_2$,
H-Asn-(Glu)$_5$-desPro$^{36}$,Pro$^{37}$,Pro$^{38}$[Met(O)$^{14}$,Asp$^{28}$]exendin-4(1-39)-NH$_2$,
desPro$^{36}$, Pro$^{37}$, Pro$^{38}$[Met(O)$^{14}$, Trp(O$_2$)$^{25}$,Asp$^{28}$]exendin-4(1-39)-(Lys)$_6$-NH$_2$,
H-(Lys)$_6$-desPro$^{36}$,Pro$^{37}$,Pro$^{38}$[Met(O)$^{14}$,Trp(O$_2$)$^{25}$,Asp$^{28}$] exendin-4(1-39)-(Lys)$_6$-NH$_2$,
H-Asn-(Glu)$_5$-desPro$^{36}$,Pro$^{37}$,Pro$^{38}$[Met(O)$^{14}$,Trp(O$_2$)$^{25}$, Asp$^{28}$]exendin-4(1-39)-(Lys)$_6$-NH$_2$, and pharmaceutically acceptable salts thereof.

In a further aspect a preferred GLP-1 agonist is selected from the group consisting of GLP-1 (in particular GLP-1 (7-36) amide, SEQ ID NO:4), Arg$^{34}$,Lys$^{26}$(N$^E$(γ-glutamyl (N$^α$hexadecanoyl)))GLP-1 (7-37) (liraglutide), albiglutide, dulaglutide, semaglutide and pharmaceutically acceptable salts thereof. In particular, a preferred GLP-1 agonist is selected form the group consisting of albiglutide, dulaglutide, semaglutide and pharmaceutically acceptable salts thereof.

A further preferred GLP-1 agonist is lixisenatide (SEQ ID NO:1) as well as its pharmaceutically acceptable salts.

In one aspect the polypeptide to be synthesized is preferably lixisenatide or exendin-4, wherein, after coupling of the amino acid building block Arg(20), Glu (17), Gln(13), Leu(10) or/and Gly(4), step (b) is performed for about 10 min with a capping reagent comprising 2% v/v acetic anhydride and 1% v/v diisopropylethylamine.

In one aspect the method according to the invention comprises the synthesis of a polypeptide in form of a solid phase synthesis. The method according to the invention optionally comprises a further step of:
(d) cleaving the polypeptide linked to the solid phase.

Step (d) is particularly performed when the synthesis of the amino acid chain is completed. Step (d) can be performed by cleavage of a solid phase-bound polypeptide from the solid phase, comprising contacting the solid phase, to which the polypeptide is bound, with a composition consisting essentially of trifluoroacetic acid and 1,2-ethanedithiol, at a temperature in the range of about 23° C. to about 29° C.

Cleavage can be performed with a composition comprising trifluoroacetic acid in an amount of about 95 to about 99% v/v.

Cleavage can also be performed with a composition comprising 1,2-ethanedithiol in an amount of about 1 to about 5% v/v.

Preferably, cleavage is performed with a composition essentially consisting of trifluoroacetic acid in an amount of about 97% v/v, and 1,2-ethanedithiol in an amount of about 3% v/v.

Cleavage can be performed by contacting the composition with the solid phase to which the polypeptide is bound, at a temperature of about 25° C. to about 27° C.

Preferably, cleavage is performed by contacting the composition with the solid phase to which the polypeptide is bound, at a temperature of about 26° C.

Most preferably, cleavage is performed with a composition essentially consisting of trifluoroacetic acid in an amount of about 97% v/v, and 1,2-ethanedithiol in an amount of about 3% v/v, at a temperature of about 26° C.

Most preferably, cleavage is performed with a composition essentially consisting of trifluoroacetic acid in an amount of about 97% v/v, and 1,2-ethanedithiol in an amount of about 3% v/v, at a temperature of about 26° C. for about 4 h.

A preferred aspect of the invention relates to a method for the solid phase synthesis of a polypeptide comprising a pre-determined amino acid sequence, the method comprising coupling cycles of amino acid building blocks to an amino acid chain, wherein said amino acid building blocks comprise an unprotected C-terminal carboxyl group and a protected N-terminal amino group, and wherein said amino acid chain comprises an unprotected N-terminal amino group, wherein at least one coupling cycle comprises the steps:
(a) coupling the amino acid building block C-terminally at the unprotected N-terminal amino group of the amino acid chain, so that an amide bond is formed between the amino acid chain and the amino acid building block,
(b) contacting the product obtained in step (a) with a capping reagent comprising acetic anhydride, wherein the acetic anhydride binds to an unprotected N-terminal amino group of the amino acid chain to which no building block has been coupled in step (a), and
(c) de-protecting the N-terminal amino group of the amino acid building block, wherein the capping reagent comprises 0.5-5% v/v of acetic anhydride, and 0.2-2% v/v of diisopropylethylamine.

A further aspect of the present invention relates to a composition comprising 0.5-5% v/v of acetic anhydride and 0.2-2% v/v of diisopropylethylamine in DMF. In a preferred aspect the composition according to the invention comprises 1-3% v/v of acetic anhydride and 0-5-2% v/v diisopropylethylamine in DMF, preferably about 2% v/v acetic anhydride and about 1% v/v diisopropylethylamine in DMF.

Yet another aspect of the present invention relates to a composition comprising diisopropylethylamine in a concentration of about 1% v/v, and acetic anhydride in a concentration of about 2% v/v.

Yet another aspect of the invention relates to a composition comprising a homologue of acetic anhydride in a concentration of 0.5-5% v/v. In a preferred aspect the concentration of the acetic anhydride homologue is 1-3% v/v, more preferably about 2% v/v. The composition can comprise DIPEA, as described herein.

Yet another aspect of the invention relates to a composition comprising benzoyl chloride in a concentration of 0.5-5% v/v. In a preferred aspect the concentration of benzoyl chloride is 1-3% v/v, more preferably about 2% v/v. The composition can comprise DIPEA, as described herein.

Yet another aspect of the invention relates to a composition comprising N-(benzyloxycarbonyloxy)succinimide in a concentration of 0.5-5% v/v. In a preferred aspect the concentration of N-(benzyloxycarbonyloxy)succinimide is 1-3% v/v, more preferably about 2% v/v. The composition can comprise DIPEA, as described herein.

Yet another aspect of the invention relates to a composition comprising benzyl chloroformate in a concentration of 0.5-5% v/v. In a preferred aspect the concentration of benzyl chloroformate is 1-3% v/v, more preferably about 2% v/v. The composition can comprise DI PEA, as described herein.

Yet another aspect of the invention relates to a composition comprising an ester of chloroformic acid in a concentration of 0.5-5% v/v. In a preferred aspect the concentration of the ester of chloroformic acid is 1-3% v/v, more preferably about 2% v/v. The composition can comprise DIPEA, as described herein.

Yet another aspect of the invention relates to a composition comprising 1-acetylimidazole in a concentration of 0.5-5% v/v. In a preferred aspect the concentration of 1-acetylimidazole is 1-3% v/v, more preferably about 2% v/v. The composition can comprise DIPEA, as described herein.

Yet another aspect of the invention relates to a composition comprising di-tert-butyl dicarbonate in a concentration of 0.5-5% v/v. In a preferred aspect the concentration of di-tert-butyl dicarbonate is 1-3% v/v, more preferably about 2% v/v. The composition can comprise DIPEA, as described herein.

Yet another aspect of the invention relates to a capping composition comprising N-(tert-butoxycarbonyloxy)succinimide in a concentration of 0.5-5% v/v. In a preferred aspect the concentration of N-(tert-butoxycarbonyloxy)succinimide is 1-3% v/v, more preferably about 2% v/v. The composition can comprise DIPEA, as described herein.

The composition according to the invention can be used for capping of free amino groups in the synthesis of a polypeptide, in particular in the synthesis of a polypeptide as described herein. Moreover, the composition according to the invention can be used for the acetylation of a free carbon-bound amino group as described herein.

In a preferred aspect the composition according to the invention is applied in step (b) of the method according to the invention, e.g. for a period of 10 min, after coupling step (a) of positions Arg(20), Glu(17), Gln(13), Leu(10) or/and Gly(4) of lixisenatide, exendin-3 or exendin-4, or the respective positions of further GLP-1 analogue.

Yet another aspect of the invention is the use of the composition, as described herein, for acetylation of an unprotected amino group in polypeptide synthesis.

Abbreviations

Ac(N1-N2): N-terminally acetylated fragment of a polypeptide from position N1 to N2.
H(N1-N2) or (N1-N2): Fragment of a polypeptide from position N1 to N2 comprising a free, N-terminal amino function.
Fmoc(N1-N2): Fragment of a polypeptide from position N1 to N2 comprising a protected N-terminal amino function, wherein the protective group is Fmoc.
(N−1)-impurity: Relates to the occurrence of an unintended peptide during peptide synthesis, which lacks a building block at a certain position. In case the intended synthesized polypeptide has a length N, the impurity has a length of N−1. The occurrence of (N−1) impurities is prevented by capping.

Fmoc fluorenylmethoxycarbonyl
Boc tert-butoxycarbonyl
Bzl benzyl
Pbf 2,2,5,7,8-pentamethyldihydrobenzofuran-5-sulfonyl
tBu tert-butyl
OtBu O-tert-butyl
Trt trityl
DIPE diisopropylether The invention is further characterized by the following Figures and Examples.

FIGURES

FIG. 1: Solid phase synthesis of peptides.

FIG. 2: Sequence of lixisenatide (SEQ ID NO:1), exendin-4 (SEQ ID NO:2), exendin-3 (SEQ ID NO:3) and GLP-1 (GLP-1(7-36) amide, SEQ ID NO:4).

Figure 3:
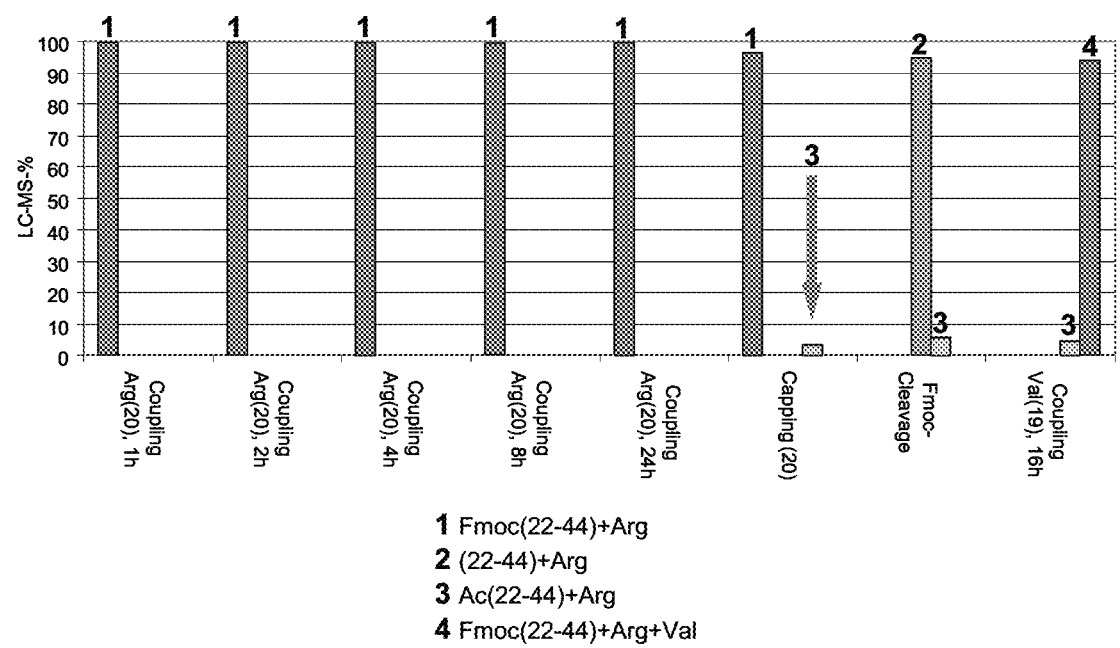

FIG. 3: Occurrence of acetylated erroneous sequences during synthesis of lixisenatide. Coupling of Fmoc-Arg(20)-OH and subsequent capping/Fmoc cleavage. It should be noted that the position 21 (Leu) was omitted from the synthesis. (1) Fmoc-(22-44)(SEQ ID NO:22)+Arg, (2) (22-44)(SEQ ID NO:22)+Arg, (3) Ac(22-44)(SEQ ID NO:22)+Arg, (4) Fmoc-(22-44)(SEQ ID NO:22)+Arg+Val. The data show that the acetylated fragments have already been formed during the capping step, however, the wrong position is acetylated [Ac(22-24)(SEQ ID NO:22)+Arg is already occurring during capping of Arg].

Figure 4:
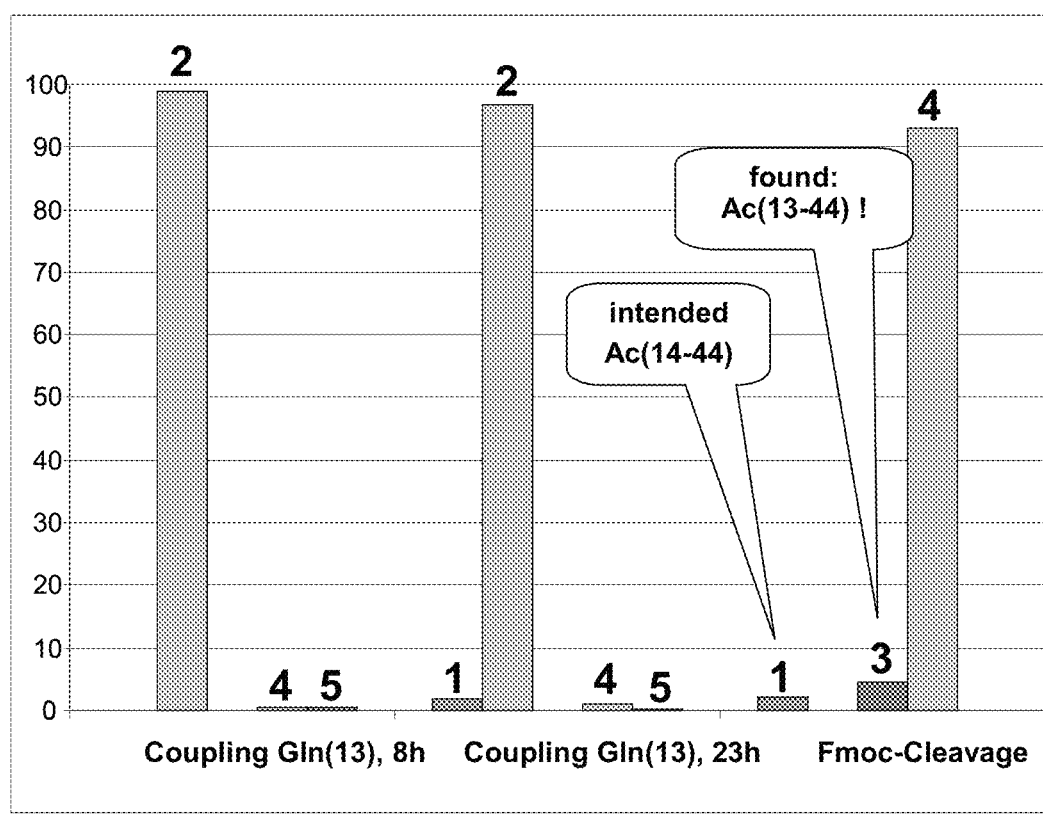

FIG. 4: Occurrence of acetylated erroneous sequences during synthesis of lixisenatide. Coupling of Fmoc-Gln(13)-OH and subsequent capping/Fmoc cleavage. (1) Ac(14-44) (SEQ ID NO:16), (2) Fmoc(13-44)(SEQ ID NO:15), (3) Ac(13-44)(SEQ ID NO:15), (4) (13-44)(SEQ ID NO:15), (5) (14-44)(SEQ ID NO:16). The data show that the acetylated fragments have already been formed during the capping step, however, the wrong position is acetylated (Ac (13-44)(SEQ ID NO:15)).

Figure 5:
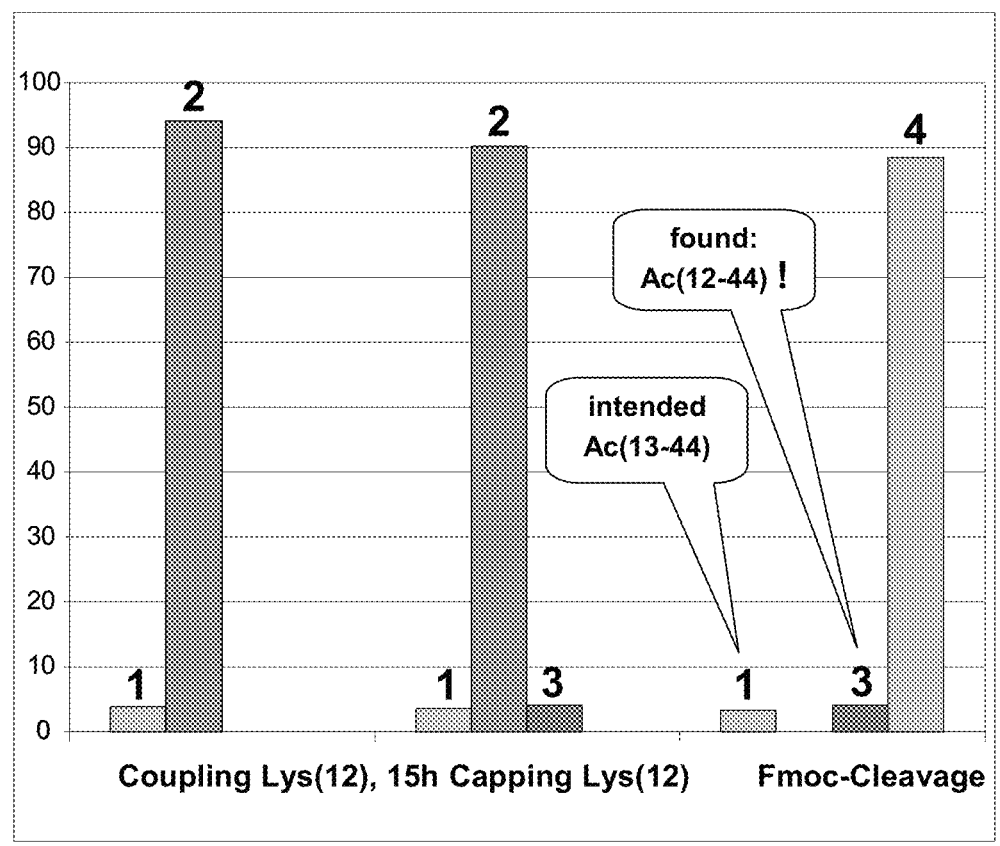

FIG. 5: Occurrence of acetylated erroneous sequences during synthesis of lixisenatide. Coupling of Fmoc-Lys(12)-OH and subsequent capping/Fmoc cleavage. (1) Ac(13-44) (SEQ ID NO:15), (2) Fmoc(12-44)(SEQ ID NO:14), (3) Ac(12-44)(SEQ ID NO:14), (4) (12-44). The data show that the acetylated fragments have already been formed during the capping step, however, the wrong position is acetylated (Ac(12-44)(SEQ ID NO:14)).

FIGS. 6A-6C: Comparison of the synthesis of lixisenatide using the method of capping according to the invention (FIG. 6B) in comparison to capping with 10% acetic anhydride and 5% v/v DI PEA in DMF for 20 min (FIG. 6A) by means of HPLC chromatography. (FIG. 6C) overlap of HPLC chromatograms of (FIG. 6A) and (FIG. 6B). Peaks labels: Ac(4-44)(SEQ ID NO:6); Ac(6-44)(SEQ ID NO:8); Ac(10-44)(SEQ ID NO:12); Ac(13-44)(SEQ ID NO:15); Ac(17-44)(SEQ ID NO:17); and (Ac(20-44)(SEQ ID NO:20).

Figure 7:
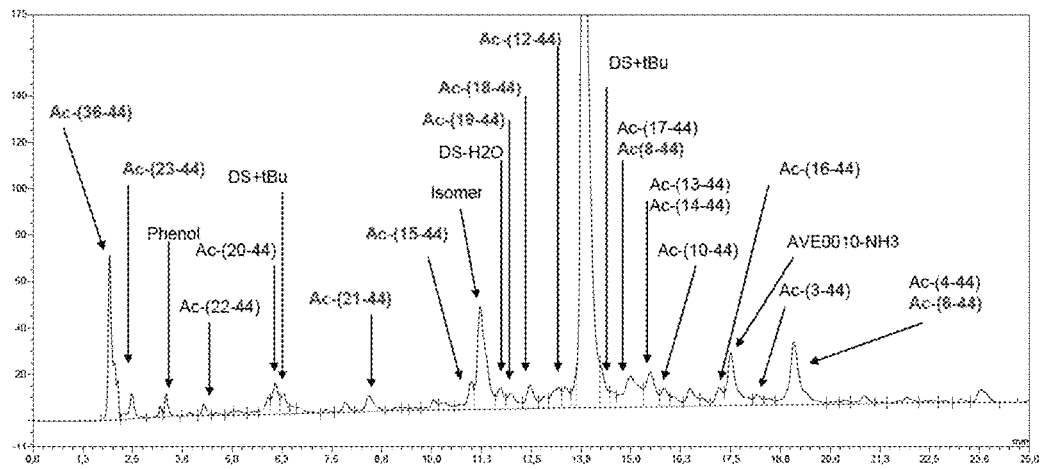

FIG. 7: HPLC of lixisenatide (raw product). Red: undesired acetylated by-products. Peak labels: Ac(3-44)(SEQ ID NO:5); Ac(4-44)(SEQ ID NO:6); Ac(6-44)(SEQ ID NO:8); Ac(8-44)(SEQ ID NO:10); Ac(10-44)(SEQ ID NO:12); Ac(12-44)(SEQ ID NO:14); Ac(13-44)(SEQ ID NO:15); Ac(14-44)(SEQ ID NO:16); Ac(15-44)(SEQ ID NO:27); Ac(16-44)(SEQ ID NO:28); Ac(17-44)(SEQ ID NO:17); Ac(18-44)(SEQ ID NO:18); Ac(19-44)(SEQ ID NO:19); (Ac(20-44)(SEQ ID NO:20); (Ac(21-44)(SEQ ID NO:21); (Ac(22-44)(SEQ ID NO:22); (Ac(23-44)(SEQ ID NO:23); and (Ac(36-44)(SEQ ID NO:26).

Figure 8:
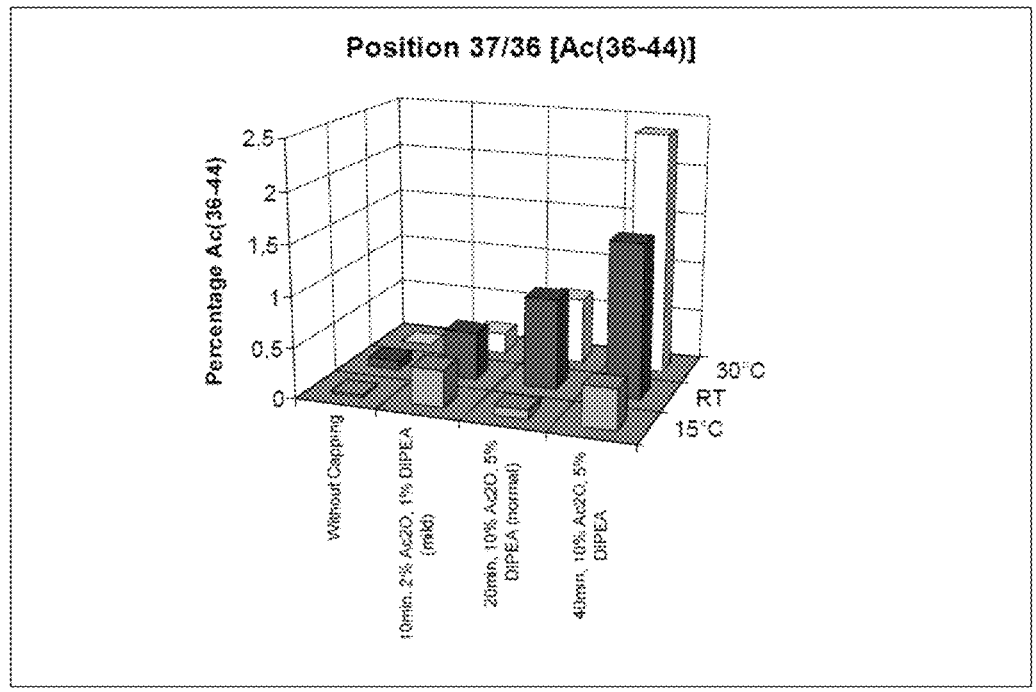

FIG. 8: Ac(36-44)(SEQ ID NO:26) formation, depending upon the capping cocktail and temperature.

Figure 9:
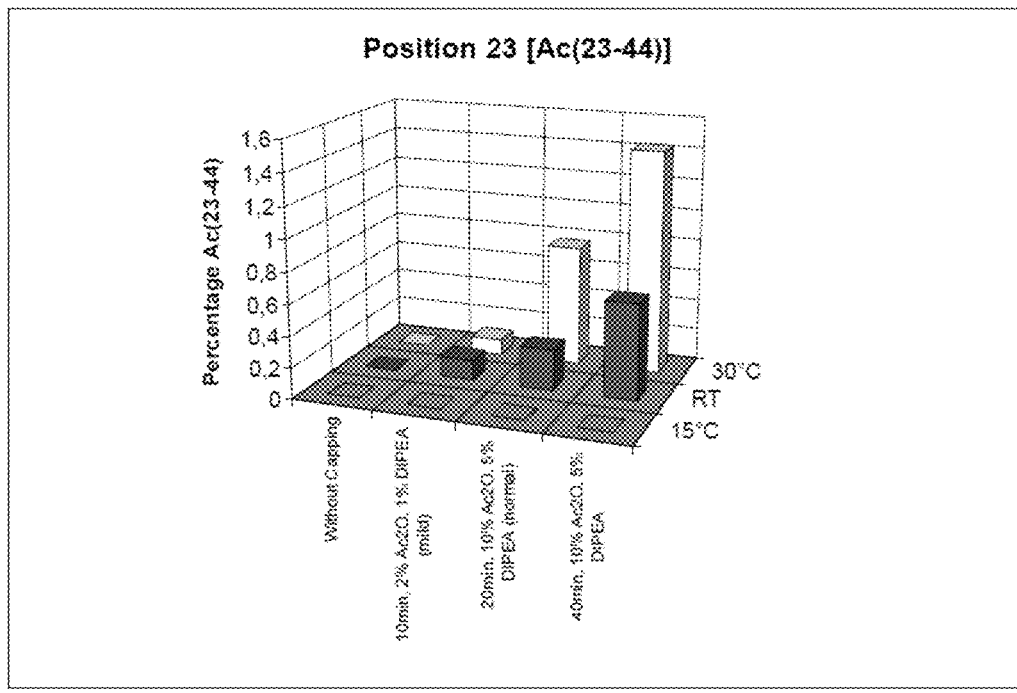

FIG. 9: Ac(23-44)(SEQ ID NO:23) formation, depending upon the capping cocktail and temperature.

Figure 10:
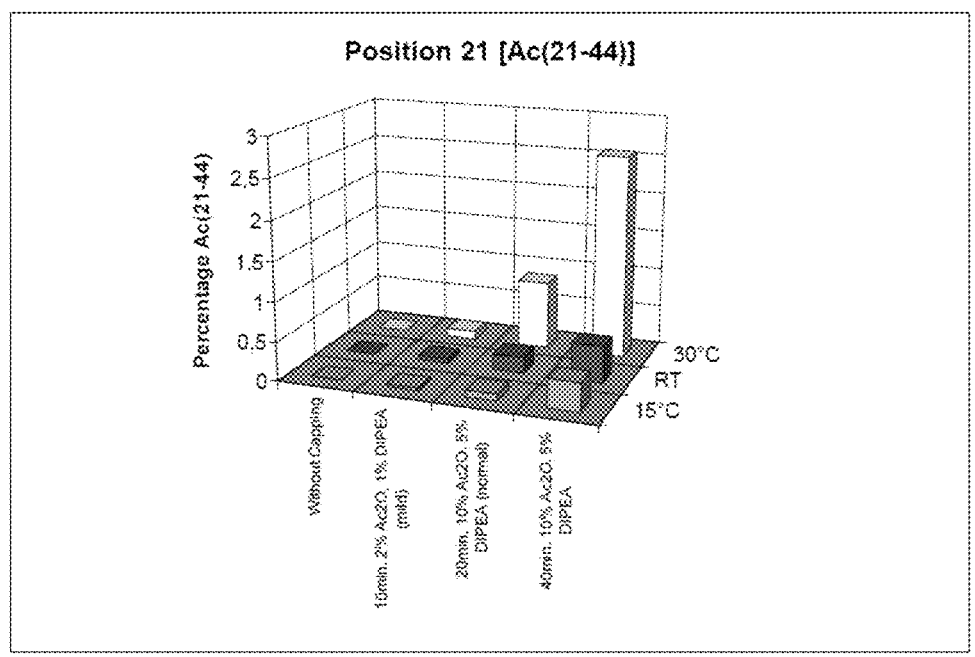

FIG. 10: Ac(21-44)(SEQ ID NO:21) formation, depending upon the capping cocktail and temperature.

Figure 11:
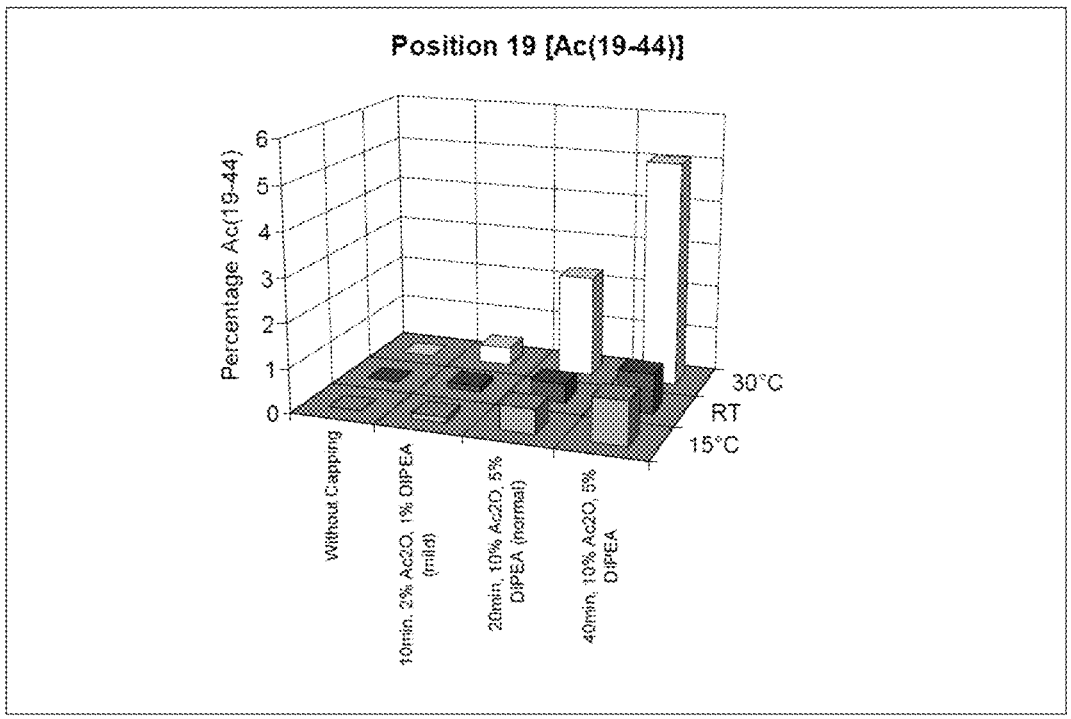

FIG. 11: Ac(19-44)(SEQ ID NO:19) formation, depending upon the capping cocktail and temperature.

Figure 12:
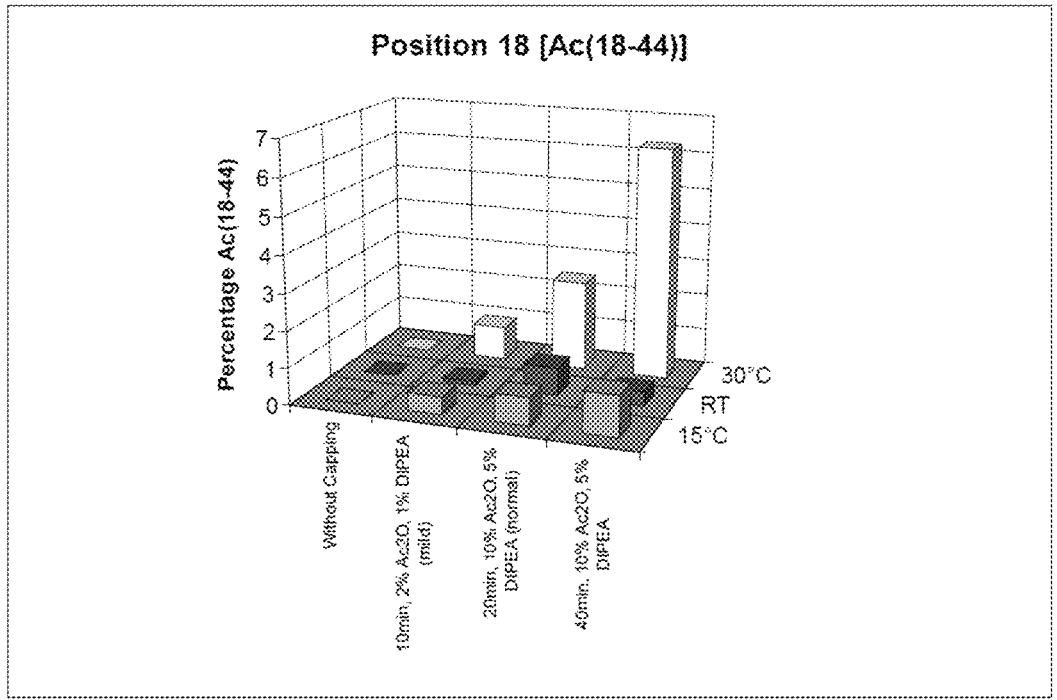

FIG. 12: Ac(18-44)(SEQ ID NO:18) formation, depending upon the capping cocktail and temperature.

Figure 13:
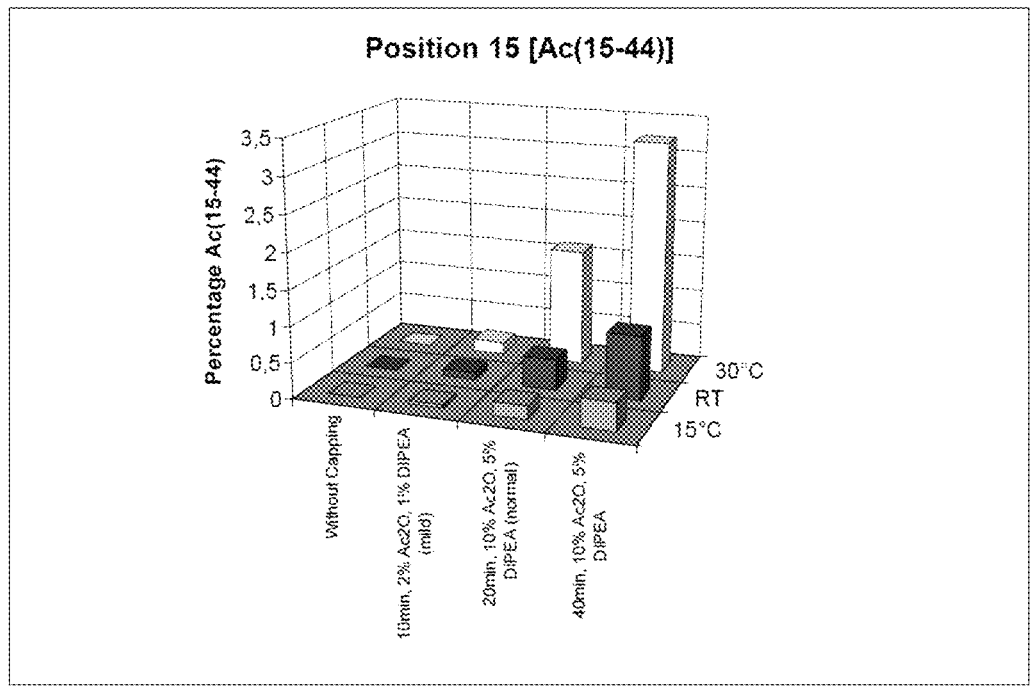

FIG. 13: Ac(15-44)(SEQ ID NO:27) formation, depending upon the capping cocktail and temperature.

Figure 14:
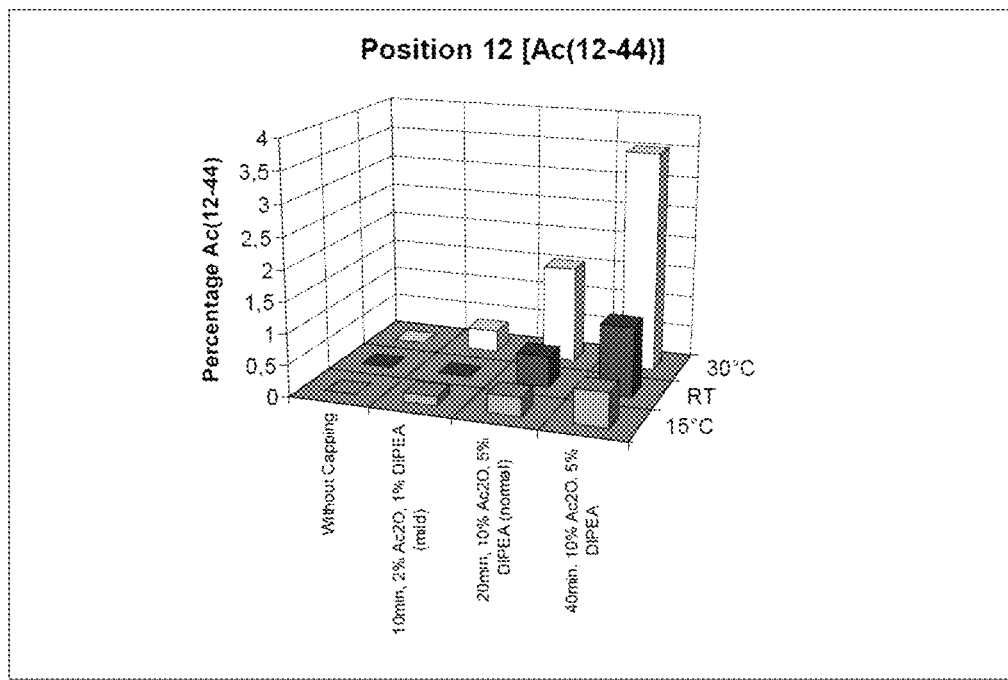

FIG. 14: Ac(12-44)(SEQ ID NO:14) formation, depending upon the capping cocktail and temperature.

Figure 15:
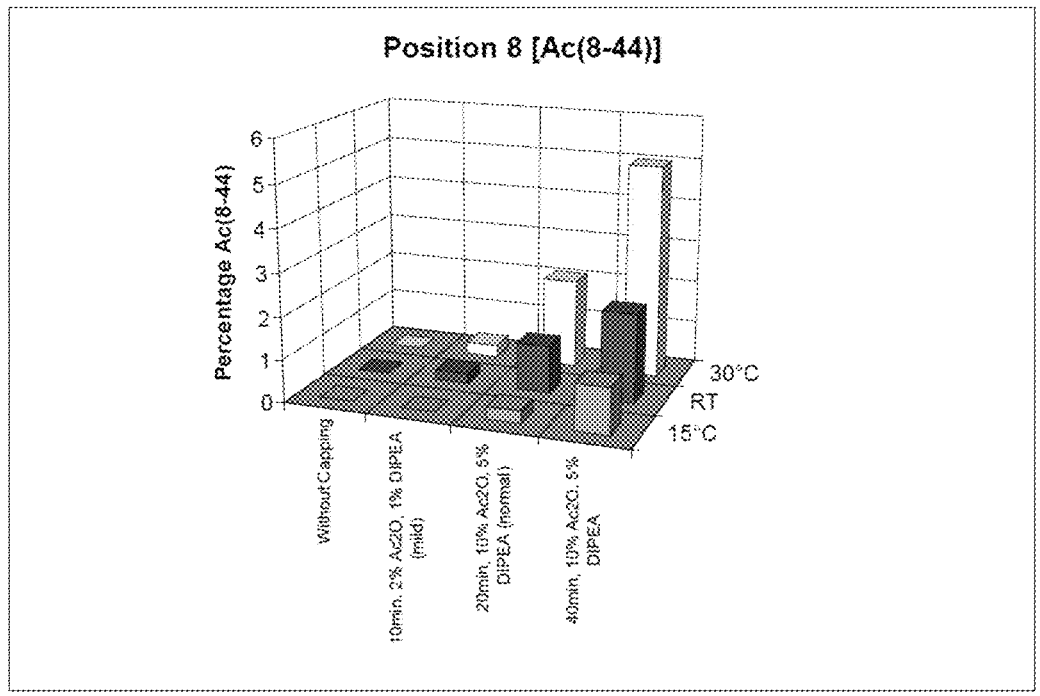

FIG. 15: Ac(8-44)(SEQ ID NO:10) formation, depending upon the capping cocktail and temperature.

Figure 16:
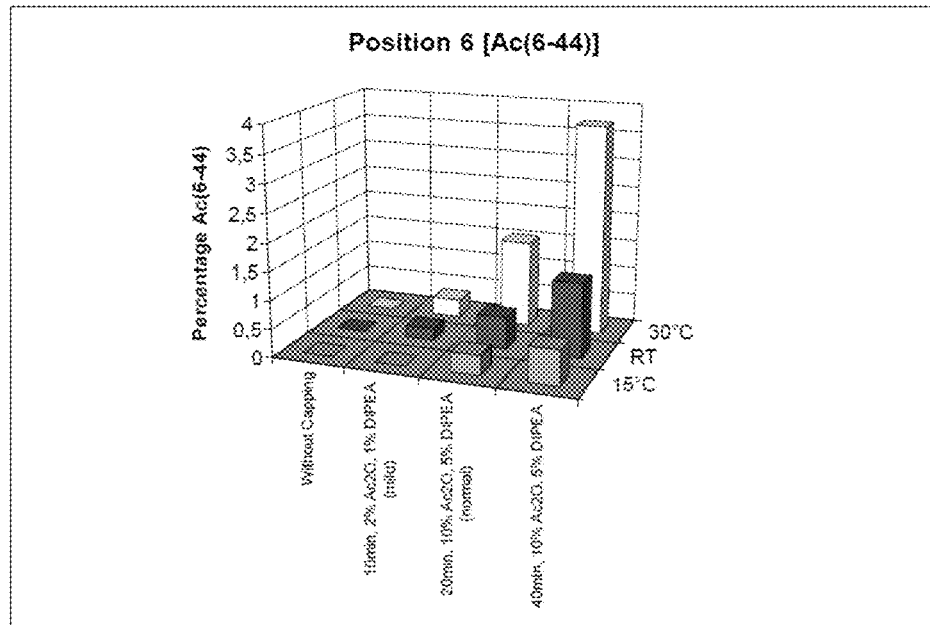

FIG. 16: Ac(6-44)(SEQ ID NO:8) formation, depending upon the capping cocktail and temperature.

Figure 17:
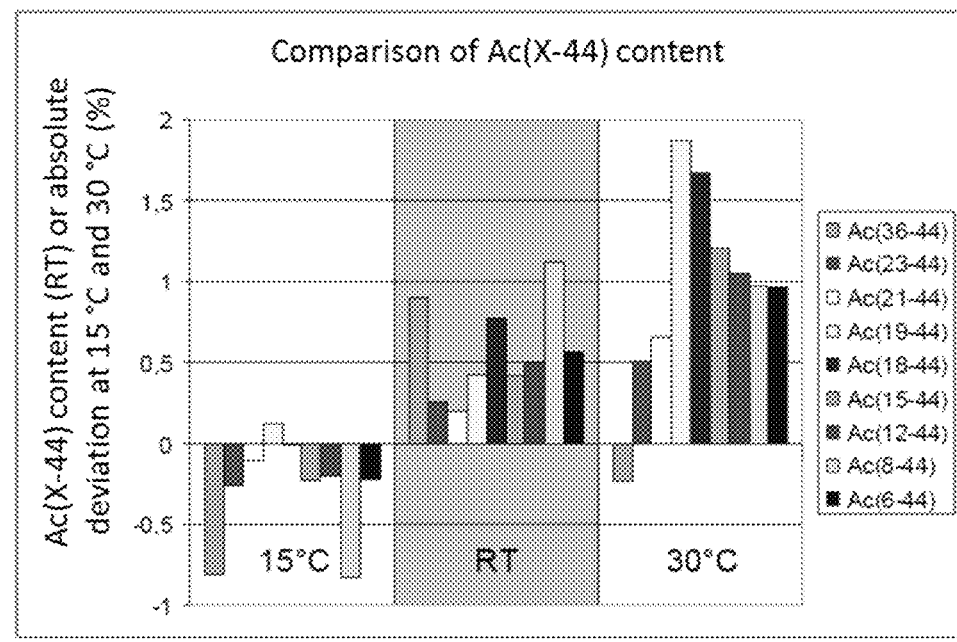

FIG. 17: Comparison of Ac(X-44) content in capping at 9 different positions in the lixisenatide synthesis at 15° C., room temperature (RT) and 30° C. Legend: Ac(6-44)(SEQ ID NO:8); Ac(8-44)(SEQ ID NO:10); Ac(12-44)(SEQ ID NO:14); Ac(15-44)(SEQ ID NO:27); Ac(18-44)(SEQ ID NO:18); Ac(19-44)(SEQ ID NO:19); (Ac(21-44)(SEQ ID NO:21); (Ac(23-44)(SEQ ID NO:23); and (Ac(36-44)(SEQ ID NO:26).

Figure 18:
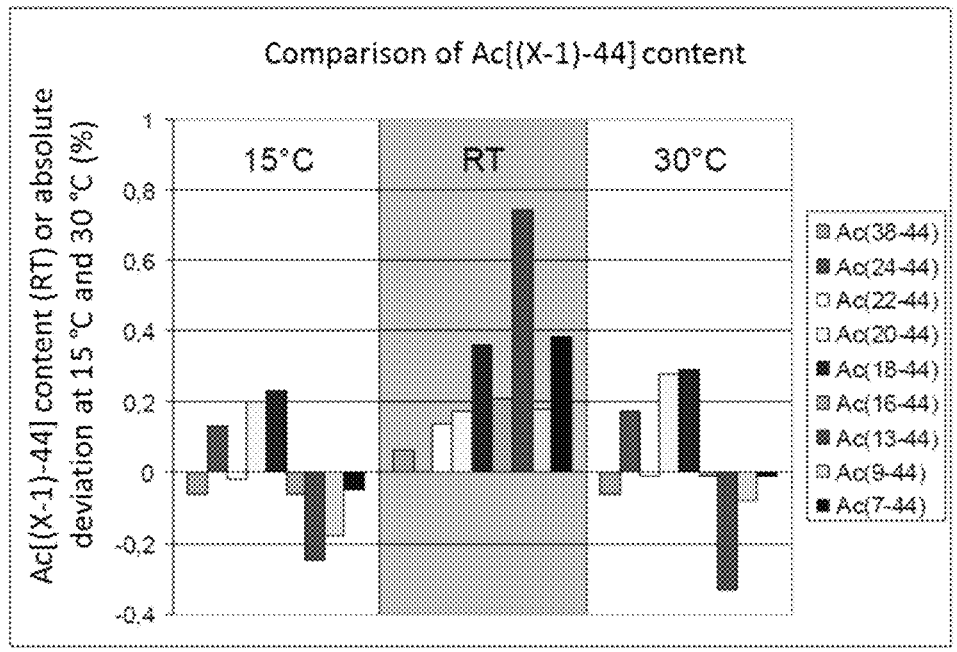

FIG. 18: Comparison of Ac[(X-1)-44] content in capping at 9 different positions in the lixisenatide synthesis at 15° C., room temperature (RT) and 30° C. Legend: Ac(7-44)(SEQ ID NO:9); Ac(9-44)(SEQ ID NO:11); Ac(13-44)(SEQ ID NO:15); Ac(16-44)(SEQ ID NO:28); Ac(18-44)(SEQ ID NO:18); Ac(20-44)(SEQ ID NO:20); (Ac(22-44)(SEQ ID NO:22); (Ac(24-44)(SEQ ID NO:29); and (Ac(38-44)(SEQ ID NO:30).

Figure 19:
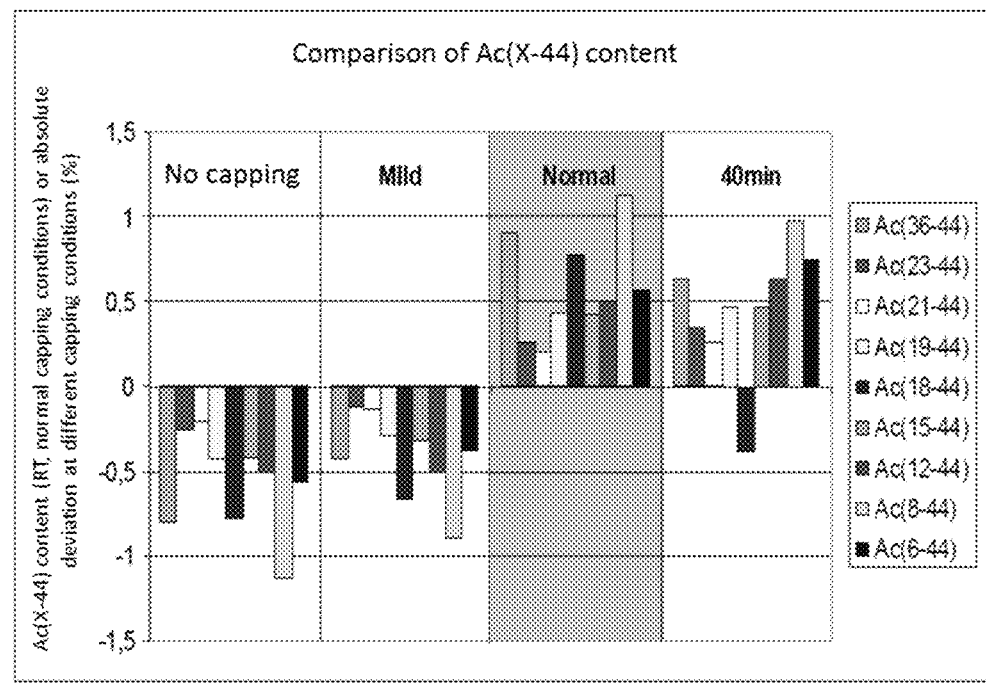

FIG. 19: Comparison of Ac(X-44) content in capping under different conditions, or without capping, at 9 different positions in the lixisenatide synthesis under different capping conditions. Legend: Ac(6-44)(SEQ ID NO:8); Ac(8-44)(SEQ ID NO:10); Ac(12-44)(SEQ ID NO:14); Ac(15-44)(SEQ ID NO:27); Ac(18-44)(SEQ ID NO:18); Ac(19-44)(SEQ ID NO:19); (Ac(21-44)(SEQ ID NO:21); (Ac(23-44)(SEQ ID NO:23); and (Ac(36-44)(SEQ ID NO:26).

Figure 20:
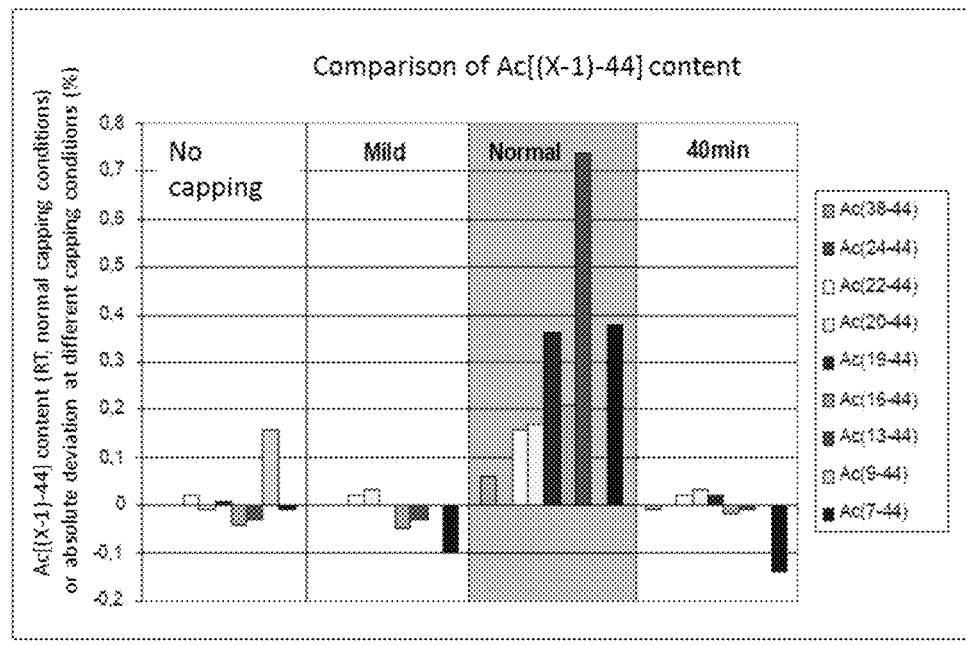

FIG. 20: Comparison of Ac[(X-1)-44] content in capping under different conditions, or without capping, at 9 different positions in the lixisenatide synthesis under different capping conditions. Legend: Ac(7-44)(SEQ ID NO:9); Ac(9-44)(SEQ ID NO:11); Ac(13-44)(SEQ ID NO:15); Ac(16-44)(SEQ ID NO:28); Ac(19-44)(SEQ ID NO:19); Ac(20-44)(SEQ ID NO:20); (Ac(22-44)(SEQ ID NO:22); (Ac(24-44)(SEQ ID NO:29); and (Ac(38-44)(SEQ ID NO:30).

EXAMPLE 1

Synthesis of Lixisenatide

The active substance Lixisenatide is a polypeptide amide composed of 44 amino acids; acetate functions as counterion.

In the one-letter code, the amino acid sequence of Lixisenatide is as follows:

H-G-E-G-T-F-T-S-D-L-S-K-Q-M-E-E-E-A-V-R-L-F-I-E-W-

L-K-N-G-G-P-S-S-G-A-P-P-S-K-K-K-K-K-K-NH$_2$

The peptide chain was constructed by means of linear solid-phase synthesis, starting from the C-terminus, Lys-44.

The method of synthesis is Fmoc solid-phase peptide synthesis, in which a Rink amide resin was used in order to obtain a peptide amide. The reactions were carried out in DMF at room temperature. Between the reactions, washing was carried out repeatedly, mostly with DMF, with one of the middle washing steps being carried out with isopropanol.

The synthesis of Lixisenatide on the polymeric support can be broken down into the following steps:
Coupling of the first Fmoc-amino acid (Fmoc-Lys(Boc)-OH) to Rink resin
Capping of the unreacted amino group
Cleavage of the temporary protecting group Fmoc
Coupling of the further Fmoc-amino acids or Fmoc-dipeptides
Capping of the unreacted amino group
Final Fmoc cleavage
Cleavage of Lixisenatide from the resin and simultaneous removal of the side chain protecting groups The synthesis cycle is illustrated in FIG. 1.

1.1 Coupling of the First Fmoc-Amino Acid (Fmoc-Lys(Boc)-OH) to Rink Resin

Before the synthesis began, the Rink amide resin was swollen in DMF. The swelling was carried out for 2-15 h. Subsequently, the temporary protecting group Fmoc was cleaved from the Rink amide resin using 25% piperidine in DMF. This cleavage was undertaken twice; cleavage time of 5 minutes and 20 minutes. Following the Fmoc cleavage, the resin was washed repeatedly with DMF and once with isopropanol.

The coupling of the first Fmoc-amino acid, Fmoc-Lys(Boc)-OH, was carried out in an excess of 2.4 eq, in order to load the resin. HOBt hydrate, HBTU and DIPEA served as coupling reagents. The coupling time was 60-120 min.

In order to completely load the Rink resin with Fmoc-Lys(Boc)-OH, a further loading was carried out with the coupling reagents HOBt hydrate and DIC. The coupling time was 6-18 h. The mixture was stirred while step 1.1 was carried out. The capping was subsequently carried out.

1.2 Capping of the Unreacted Amino Group

The consequence of incomplete loading of the resin is that as yet unreacted amino groups are found on the resin. These were inactivated, and hence made unavailable for further coupling, by adding a mixture of acetic anhydride/DIPEA/DMF (10:5:85). The capping mixture remained on the resin for 20 minutes while stirring. The remaining free amino group is acylated. Subsequently, the resin was washed repeatedly with DMF and once with isopropanol.

A capping method according to the invention at least at 5 positions of a Lixisenatide synthesis is described in examples 4 and 5.

1.3. Cleavage of the Temporary Protecting Group Fmoc

The temporary protecting group Fmoc was cleaved using 25% piperidine in DMF. This cleavage was undertaken twice; cleavage time of 5 minutes and 20 minutes. Following the Fmoc cleavage, the resin was washed repeatedly with DMF and once with isopropanol.

1.4 Coupling of the Further Fmoc-Amino Acids or Fmoc-Dipeptides

The next Fmoc-amino acid was coupled to the deprotected amino group on the resin. The coupling was carried out in DMF at different equivalents. The coupling times were between 2 h and 18 h. HOBt/DIC, and also HBTU/DIPEA, were used as coupling reagents.

The following derivatives were used as Fmoc-amino acids:
Fmoc-Lys(Boc)-OH
Fmoc-Ser(tBu)-OH
Fmoc-Pro-OH
Fmoc-Ala-OH×$H_2O$
Fmoc-Gly-OH
Fmoc-Asn(Trt)-OH
Fmoc-Leu-OH
Fmoc-Trp(Boc)-OH
Fmoc-Glu(OtBu)-OH×$H_2O$
Fmoc-Ile-OH
Fmoc-Phe-OH
Fmoc-Arg(Pbf)-OH
Fmoc-Val-OH
Fmoc-Met-OH
Fmoc-Gln(Trt)-OH
Fmoc-Asp(OtBu)-OH
Fmoc-Thr(tBu)-OH
Fmoc-His(Trt)-OH Alternatively, it was also possible to use Fmoc-dipeptides (method according to the invention):
Fmoc-Pro-Pro-OH (CAS 129223-22-9)
Fmoc-Ala-Pro-OH (CAS 186023-44-9)
Fmoc-Ser(tBu)-Gly-OH (CAS 113247-80-6)
Fmoc-Gly-Pro-OH (CAS 212651-48-4)
Fmoc-Gly-Gly-OH (CAS 35665-38-4)
Fmoc-Asn(Trt)-Gly-OH (from Bachem B-3630)
Fmoc-Glu(OtBu)-Gly-OH (CAS 866044-63-5)
Fmoc-His(Trt)-Gly-OH If the coupling was found to be incomplete according to the Kaiser test (E. Kaiser et al, Anal. Biochem. 34, 1970, 595), further coupling was possible. For this purpose, the Fmoc-amino acid was coupled again, together with HBTU/DIPEA/HOBt hydrate.

1.5 Capping of the Unreacted Amino Group

See description under point 1.2.

1.6 Final Fmoc Cleavage

The final Fmoc cleavage was carried out as described under point 1.3. The resin was finally washed again with diisopropyl ether and dried under reduced pressure.

1.7 Cleavage of Lixisenatide from the Resin and Simultaneous Removal of the Side Chain Protecting Groups The cleavage of Lixisenatide from the Rink resin was carried out as described in example 6.

1.8 Synthesis of Lixisenatide with Inventive Use of Dipeptides

The coupling of the first Fmoc-Lys(Boc)-OH to the resin was carried out with HBTU/DIPEA/HOBt hydrate. After the coupling of the first amino acid Fmoc-Lys(Boc)-OH to the free amine of the Rink amide resin, the following process steps were conducted in an endlessly repeating cycle (see also steps 1.3 to 1.6):
Fmoc cleavage
Coupling
Further coupling, if necessary
Capping
After coupling of the final amino acid unit, the N-terminal Fmoc group is cleaved.

Standard Fmoc-protected amino acids were coupled with DIC/HOBt, with the excess of amino acids and coupling reagents being between 2 and 4 equivalents.

At the positions Pro(36) and Pro(37), instead of two Fmoc-Pro-OH amino acid derivatives, the dipeptide Fmoc-Pro-Pro-OH was coupled with HBTU/DIPEA.

At the position Pro(31), coupling was carried out with HBTU/DIPEA/HOBt hydrate.

At the positions His(1) and Gly(2), instead of the amino acid derivatives Fmoc-His(Boc)-OH and Fmoc-Gly-OH, the dipeptide Fmoc-His(Trt)-Gly-OH was coupled.

After the couplings, the capping was carried out in each case with Ac₂O/DIPEA, as is described in examples 4 and 5.

The Fmoc cleavage was performed with 25% piperidine in DMF, in each case successively first with 5 minutes of reaction time, then with 20-40 minutes of reaction time.

The completeness of the coupling was checked by means of a Kaiser test.

After the last coupling and last cleavage of the Fmoc group, the resin was washed, firstly repeatedly with DMF, then with isopropanol and finally with diisopropyl ether, and it was subsequently dried at 35° C. under reduced pressure.

The cleavage of the raw peptide from the resin was carried out in trifluoroacetic acid with scavengers such as 1,2-ethanedithiol.

The raw peptide was purified in a two-step HPLC process with C18 RP silica gel as solid phase. In the first purification step, a buffer system with acetonitrile/water with 0.1% TFA was used; in the second step, a buffer system with acetonitrile/water with AcOH was used. After concentration of the pooled solutions, the pure peptide was obtained by freeze-drying.

Use of 3500 g of Rink amide resin with a loading of 0.3 mmol/g (i.e. a 1.05 mol batch) gave 9970 g of peptide on resin. 4636 g of raw peptide were obtained therefrom.

After purification, 576 g of pure peptide were obtained therefrom. MS: 4855.5 (monoisotopic molar mass); found 4855.6. Amino acid sequencing: correct sequence found. Assay: 89.0% (as is).

1.9 Synthesis of Lixisenatide without Use of Dipeptides

The peptide chain was constructed by means of linear solid-phase synthesis, starting from the C-terminus, Lys-44.

Standard Fmoc-protected amino acids were coupled with DIC/HOBt, with the excess of amino acids and coupling reagents being between 2 and 4 equivalents.

At the positions Pro(37), Pro(36), Pro(31), coupling was carried out with HBTU/DIPEA/HOBt hydrate.

Each coupling was followed by capping with Ac₂O/DIPEA. The Fmoc cleavage was performed with 25% piperidine in DMF, in each case successively first with 5 minutes of reaction time, then with 20 minutes of reaction time.

The completeness of the coupling was checked by means of a Kaiser test. After the last coupling and last cleavage of the Fmoc group, the resin was washed, firstly repeatedly with DMF, then with isopropanol and finally with diisopropyl ether, and it was subsequently dried at 35° C. under reduced pressure.

The cleavage of the raw peptide from the resin was carried out in trifluoroacetic acid with scavengers such as 1,2-ethanedithiol, thioanisole, phenol and water.

The raw peptide was purified in a two-step HPLC process with C18 RP silica gel as solid phase. After concentration of the pooled solutions, the pure peptide was obtained by freeze-drying. Table 1 compares the contents of racemized D-His-Lixisenatide and the contents of some impurities in the pure peptide between the synthesis using the dipeptides and without the dipeptides.

TABLE 1

Comparison of the Lixisenatide syntheses with and without use of the dipeptides.

| | Content of D-His | Content of desGly(2)-Lixisenatide | Content of desPro(36)-Lixisenatide | Content of diPro(36)-Lixisenatide |
|---|---|---|---|---|
| Synthesis of lixisenatide with dipeptides Fmoc-His(Trt)-Gly-OH, Fmoc-Pro-Pro-OH according to the invention | 0.41% | Not present | Not present | Not present |
| Comparative synthesis of lixisenatide without dipeptides | 4.1% | 2.5% | 1% | 1% |

The data show that the use of the dipeptide Fmoc-His(Trt)-Gly-OH gives a Lixisenatide which does not contain elevated values of D-His arising from racemization. Moreover, when using Fmoc-His(Trt)-Gly-OH, desGly(2)-Lixisenatide is no longer found. Furthermore, the N−1 and N+1 peptides in the vicinity of the chain position Pro(36) and Pro(37) (e.g. desPro(36)-Lixisenatide or diPro(36)Lixisenatide) did not occur.

EXAMPLE 2

Synthesis, Purification and Characterization of Exendin-4 (According to the Invention)

The active substance Exendin-4 is a polypeptide amide composed of 39 amino acids; acetate functions as counterion.

In the one-letter code, the amino acid sequence is as follows:

H-G-E-G-T-F-T-S-D-L-S-K-Q-M-E-E-A-V-R-L-F-I-E-W-

L-K-N-G-G-P-S-S-G-A-P-P-P-S-NH₂

MW 4186.66 g/mol; MW (monoisotopic)=4184.03 g/mol.

The synthesis of Exendin-4 was carried out precisely as described in the synthesis of Lixisenatide, according to the abovementioned sequence. At positions 1 and 2, coupling was carried out in one cycle with Fmoc-His(Trt)-Gly-OH. At positions 37 and 38, coupling was carried out in one cycle with Fmoc-Pro-Pro-OH. At the other positions, coupling was carried out with Fmoc-amino acids (monoamino acid units).

Use of 26.666 g of Rink amide resin with a loading of 0.42 mmol/g (i.e. a 11.2 mmol batch) gave 74 g of peptide on resin. From this, 65 g of peptide on resin were cleaved, and 28 g of raw peptide were obtained. For the purification, from this, 21.3 g of raw peptide were used, and 4.01 g of pure peptide were obtained. MS: 4184.03 (monoisotopic molar mass): found 4185.1 [M+H]. Purity 98.25 Fl %.

The use of the dipeptides confirms the results which were obtained for Lixisenatide. The use of the dipeptide Fmoc-His(Trt)-Gly-OH gives an Exendin-4 which does not contain elevated values of D-His arising from racemization. Moreover, when using Fmoc-His(Trt)-Gly-OH, desGly(2)-Exendin-4 is no longer found. Furthermore, the N−1 and N+1 peptides in the vicinity of the chain position Pro(36) and Pro(37) (e.g. desPro(36)-Exendin-4 or diPro(36)Exendin-4) did not occur.

EXAMPLE 3

Synthesis of Fmoc-His(Trt)-Gly-OH

3.1 Fmoc-His(Trt)-Gly-OBzl

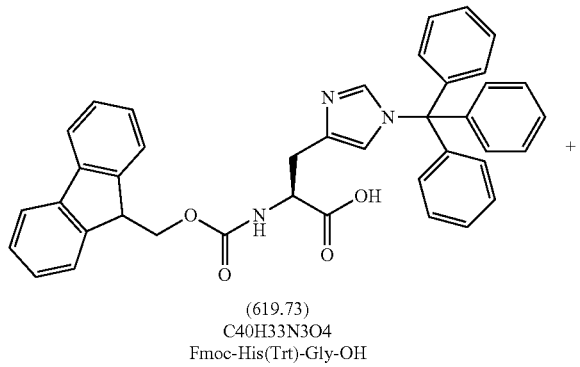

(619.73)
C40H33N3O4
Fmoc-His(Trt)-Gly-OH

+

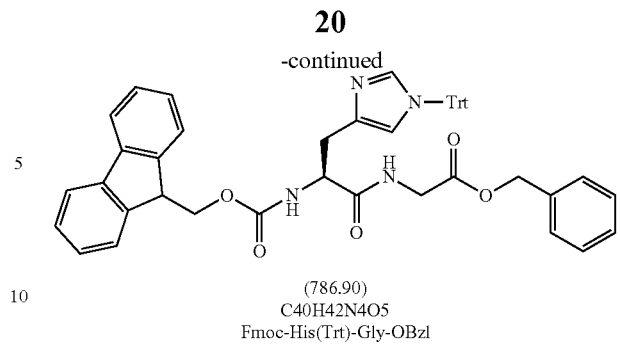

(786.90)
C40H42N4O5
Fmoc-His(Trt)-Gly-OBzl 40 g of Fmoc-His(Trt)-OH were dissolved together with 32.7 g of H-Gly-OBzl tosylate and 29.37 g of HBTU in 400 ml of ethyl acetate. Thereafter, 33.32 ml of N-ethylmorpholine were added. The reaction was stirred for 4 h at 30° C. Thereafter, extraction was carried out three times with 256 g of an 8% sodium bicarbonate solution each time, and then washing was carried out once with 250 ml of water. Half of the resulting ethyl acetate solution was evaporated and processed further in the next step.

3.2 Fmoc-His(Trt)-Gly-OH

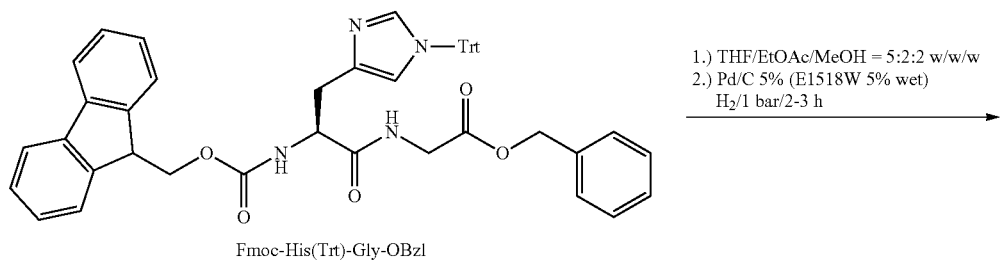

Fmoc-His(Trt)-Gly-OBzl

1.) THF/EtOAc/MeOH = 5:2:2 w/w/w
2.) Pd/C 5% (E1518W 5% wet)
H₂/1 bar/2-3 h
⟶

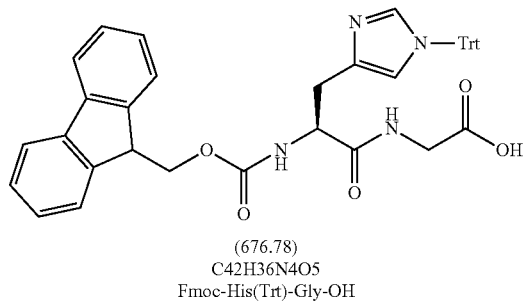

(676.78)
C42H36N4O5
Fmoc-His(Trt)-Gly-OH

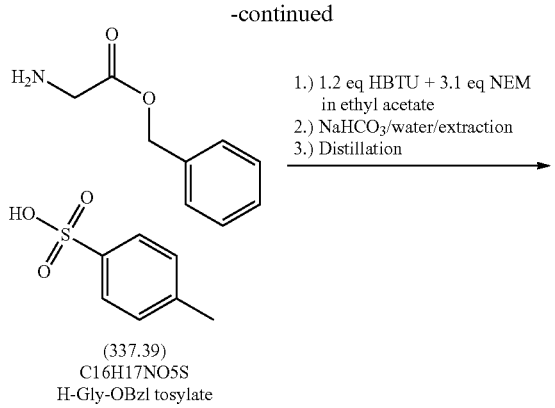

(337.39)
C16H17NO5S
H-Gly-OBzl tosylate

1.) 1.2 eq HBTU + 3.1 eq NEM in ethyl acetate
2.) NaHCO₃/water/extraction
3.) Distillation
⟶

THF and methanol were added to the ethyl acetate phase, such that a 5:2:2 (w/w/w) THF/ethyl acetate/MeOH mixture was formed. Subsequently, 10 g of palladium on carbon catalyst (5%) were added, and this mixture was hydrogenated at 30° C. and a hydrogen pressure of 1.1 bar for 2.5 h. Thereafter, the catalyst was filtered off and the resulting solution was evaporated until a precipitate began to form. Subsequent stirring was carried out for 1 h and the solution was left to stand at room temperature for 4 days. The product was filtered off and subsequently extracted by stirring in 2-butanone at 80° C. for 4 h. Yield: 32.9 g of Fmoc-His(Trt)-Gly-OH (75%).

EXAMPLE 4

Acetylated Erroneous Sequences During the Synthesis of Lixisenatide 4.1 Determining the Content of Acetylated Erroneous Sequences During the Synthesis of Lixisenatide Some acetylated erroneous sequences can be seen in the HPLC profile of the crude Lixisenatide product. These usually arise from unreacted amino groups on the resin being capped. What is achieved by the capping is that no (N−1) impurities can occur, which differ only slightly from the desired product and are hence difficult to remove by purification.

The completeness and also the coupling kinetics at selected positions were monitored by Edman degradation. A resin sample was taken from the synthesis of Lixisenatide and the Fmoc group was cleaved therefrom. This resin sample was then subjected to Edman degradation and in this way it was possible to determine the ratio of coupled amino acid to the (N−1) amino acid, from which the coupling yield could be directly inferred. The results of the Edman degradation (table 2) show high coupling values. These values are so high that they cannot account for the amounts of acetylated erroneous sequences (HPLC data in table 2). This means that there must be an alternative way of forming these by-products. The elucidation of this situation will be described in the following sections.

TABLE 2

Coupling yields and contents of acetylated fragments during synthesis of Lixisenatide. The percentage contents of acetylated erroneous sequences from HPLC data and Edman results (coelution of Ac(6-44), Ac(5-44) and Ac(4-44)) are compared to one another.

| Impurity | Amino acid to be coupled | Coupling yield (Edman data) | Impurities content (HPLC) |
|---|---|---|---|
| Ac(36-44) (SEQ ID NO: 26) | Ala(35) | 99.4-99.5% | 4.7% |
| Ac(23-44) (SEQ ID NO: 23) | Phe(22) | >98.4% | 0.9% |
| Ac(20-44) (SEQ ID NO: 20) | Val(19) | 99.7% | 2.0% |
| Ac(13-44) (SEQ ID NO: 15) | Lys(12) | 98.7-99.5% | 2.1% |
| Ac(6-44) (SEQ ID NO: 8) | Thr(5) | 98.4-99.5% | Approx. 4.3% |
| Ac(5-44) (SEQ ID NO: 7) | Gly(4) | 99.1-99.8% | |
| Ac(4-44) (SEQ ID NO: 6) | Glu(3) | 98.2-99.4% | |

4.2 Formation of Acetylated Erroneous Sequences

In order to investigate the points in the synthesis cycle at which the acetylated erroneous sequences are formed, resin samples were taken over a coupling cycle, and the peptide was cleaved and investigated using LC-MS. These investigations were carried out at the positions of coupling of Fmoc-Arg(20)-OH and coupling of Fmoc-Gln(13)-OH.

In the coupling of Fmoc-Arg(20)-OH to the solid-phase-bonded peptide of the Lixisenatide partial sequence H(22-24), samples were taken after coupling times of 1 h, 2 h, 4 h, 8 h and 24 h and also after capping, the subsequent Fmoc cleavage and the coupling of valine(19). As can be seen in FIG. 3, the erroneous sequence Ac(22-44)(SEQ ID NO:22)+Arg occurred for the first time during the capping step (3.1%). During the capping, therefore, a small portion of the Fmoc group was cleaved (lost) and immediately acylated. In order to explain the designation Ac(22-24)+Arg, it should be noted that the position 21 (Leu) was omitted from the synthesis.

The same experiment was conducted for the coupling of Fmoc-Gln(13)-OH during the Lixisenatide synthesis (FIG. 4). In this case, the erroneous sequence Ac(13-44)(SEQ ID NO:15) was observed (4.6%) for the first time during the Fmoc cleavage after the coupling and the capping of glutamine(13). In the remaining course of the synthesis after the coupling of Fmoc-Lys(12)-OH, it can be seen that Ac(12-44)(SEQ ID NO:14) was also formed (4.1%) during the capping (see FIG. 5).

The experiment shows that it is necessary to search for capping conditions, under which the undesired formation of the acetylated erroneous sequence of the Nth amino acid (the last one coupled) is prevented, without the capping ability of the mixture used being reduced to such a significant extent that a potential (N−1) impurity is no longer capped.

4.3 Variation in the Capping Conditions

The couplings of Fmoc-Arg(20)-OH, Fmoc-Leu(10)-OH, Fmoc-Gly(4)-OH and Fmoc-Thr(5)-OH were investigated. Various capping conditions were compared to one another.

The capping conditions were varied in a laboratory synthesis of Lixisenatide. Particular attention was paid to the contents of undesired Ac(N-44) and desired Ac([N−1]-44). The conditions tested are as follows:

10% acetic anhydride/5% DIPEA in DMF for 20 minutes

10% acetic anhydride/5% DIPEA in DMF for 10 minutes

2% acetic anhydride/1% DIPEA in DMF for 20 minutes

2% acetic anhydride/1% DIPEA in DMF for 10 minutes

The investigations were carried out at the positions Arg (20), Leu(10), Thr(5) and Gly(4). The results are compiled in tables 3-6.

The data were also compared with the result of a GMP synthesis of Lixisenatide ("GMP capping" in tables 3-6). The capping conditions corresponded to the conditions 10% acetic anhydride/5% DIPEA in DMF. The contact time of the resin with the capping mixture in the GMP batch was 7-8 minutes longer, and was therefore 27-28 minutes. This arose from the longer time taken to pump the capping mixture away.

4.3.1 Coupling at Position Arg(20)

Fmoc-Arg(Pbf)-OH was coupled to Leu(21). On those chains on which no coupling took place (product H(21-44)), the product Ac(21-44)(SEQ ID NO:21) was formed by the subsequent capping. Both products Ac(20-44)(SEQ ID NO:20) and H(20-44) are formed when, during capping, the Fmoc group is undesirably cleaved (formation of H(20-44)) and acetylation occurs (formation of Ac(2044)).

It can be clearly seen in table 3 that the degree of formation of the undesired products H(20-44) and Ac(20-44)(SEQ ID NO:20) is dependent both on the capping time and on the amount of acetic anhydride and DIPEA (see Ac(20-44)(SEQ ID NO:20)% column). The highest percentage value can be seen in the GMP capping. The lowest content of Ac(20-44)(SEQ ID NO:20) is found under the conditions "2% acetic anhydride/1% DIPEA in DMF for 10 minutes".

The capping power of the various capping mixtures (and hence the original intended use) is approximately the same (see column Ac(21-44)(SEQ ID NO:21)), i.e. all capping mixtures convert H(21-44)). The mixture "2% acetic anhydride/1% DIPEA in DMF for 10 minutes" also fulfils the desired purpose of avoiding (N−1) impurities.

TABLE 3

Results of the coupling of Fmoc-Arg(Pbf)-OH at position 20. The table shows the content of acetylated and non-acetylated fragments depending on the capping conditions. The results were obtained by means of LC-MS. The data were compared with the results from a GMP synthesis ("GMP capping").

| Capping conditions | Ac(20-44) (SEQ ID NO: 20) % | Fmoc(20-44) % | H(20-44) % | H(21-44) % | Ac(21-44) (SEQ ID NO: 21) % |
|---|---|---|---|---|---|
| 10 min/2% acetic anhydride, 1% DIPEA | 0.75 | 96.48 | 0.08 | 0.66 | 2.03 |
| 10 min/10% acetic anhydride, 5% DIPEA | 0.92 | 95.87 | 0.55 | 0.69 | 1.96 |
| 20 min/2% acetic anhydride, 1% DIPEA | 1.63 | 95.83 | 0.14 | 0.55 | 1.85 |
| 20 min/10% acetic anhydride, 5% DIPEA | 2.26 | 95.32 | 0.06 | 0.60 | 1.77 |
| GMP capping | 2.64 | 94.47 | 0.03 | 0.68 | 2.18 |

4.3.2 Coupling at the Positions Leu(10), Gly(4) and Thr(5)

The results for Leu(10) are given in table 4 and confirm the results which were obtained for position Arg(20). The content of undesired products Ac(10-44)(SEQ ID NO:12) and H(10-44), which are formed during the capping of the free amino groups of the product H(11-44), is lowest under the conditions "2% acetic anhydride, 1% DIPEA for 10 minutes". The capping power is comparable in the different capping mixtures.

TABLE 4

Results of the coupling of Fmoc-Leu-OH at position 10. The table shows the content of acetylated and non-acetylated fragments depending on the capping conditions. The results were obtained by means of LC-MS.

| Capping conditions | Ac(10-44) (SEQ ID NO: 12) % | Fmoc(10-44) % | H(10-44) % | H(11-44) % | Ac(11-44) (SEQ ID NO: 13) % |
|---|---|---|---|---|---|
| 10 min/2% acetic anhydride, 1% DIPEA | 0.06 | 98.90 | 0.42 | 0.18 | 0.43 |
| 10 min/10% acetic anhydride, 5% DIPEA | 0.20 | 98.57 | 0.61 | 0.16 | 0.46 |
| 20 min/2% acetic anhydride, 1% DIPEA | 0.13 | 98.24 | 0.90 | 0.18 | 0.56 |
| 20 min/10% acetic anhydride, 5% DIPEA | 0.45 | 98.44 | 0.52 | 0.15 | 0.44 |

For the coupling of Gly(4) as well, the contents of the undesired products Ac(4-44)(SEQ ID NO:6) are dependent on the capping mixture and the reaction time. The capping power is the same in the different mixtures (table 5).

TABLE 5

Results of the coupling of Fmoc-Gly-OH at position 4. The table shows the content of acetylated and non-acetylated fragments depending on the capping conditions. The results were obtained by means of LC-MS.

| Capping conditions | Ac(4-44) (SEQ ID NO: 6) % | Fmoc(4-44) % | H(4-44) % | H(6-44) % | Ac(5-44) (SEQ ID NO: 7) % |
|---|---|---|---|---|---|
| 10 min/2% acetic anhydride, 1% DIPEA | 0.09 | 98.21 | 0.55 | 0.56 | 0.61 |
| 10 min/10% acetic anhydride, 5% DIPEA | 0.26 | 98.42 | 0.39 | 0.41 | 0.52 |
| 20 min/2% acetic anhydride, 1% DIPEA | 0.10 | 98.40 | 0.47 | 0.36 | 0.67 |
| 20 min/10% acetic anhydride, 5% DIPEA | 0.39 | 98.02 | 0.43 | 0.39 | 0.77 |
| GMP capping | 0.92 | 97.54 | 0.51 | 0.40 | 0.63 |

In addition to the positions Arg(20), Leu(10) and Gly(4), the position Thr(5) was also investigated. In contrast to the three former positions, the contents of the undesired product Ac(N−44) (Ac(5-44)(SEQ ID NO:7) at position 5) are approximately the same under the various capping conditions. However, the capping power of the different mixtures is also comparable here (table 6).

TABLE 6

Results of the coupling of Fmoc-Thr(tBu)-OH at position 5. The table shows the content of acetylated and non-acetylated fragments depending on the capping conditions. The results were obtained by means of LC-MS.

| Capping conditions | Ac(5-44) (SEQ ID NO: 7) % | Fmoc(5-44) % | H(5-44) % | H(6-44) % | Ac(6-44) (SEQ ID NO: 8) % |
|---|---|---|---|---|---|
| 10 min/2% acetic anhydride, 1% DIPEA | 0.04 | 97.80 | 0.33 | 0.24 | 1.58 |
| 10 min/10% acetic anhydride, 5% DIPEA | 0.07 | 97.93 | 0.15 | 0.24 | 1.61 |
| 20 min/2% acetic anhydride, 1% DIPEA | 0.03 | 97.69 | 0.36 | 0.23 | 1.70 |
| 20 min/10% acetic anhydride, 5% DIPEA | 0.03 | 97.70 | 0.42 | 0.29 | 1.55 |
| GMP capping | 0.07 | 97.77 | 0.25 | 0.24 | 1.67 |

4.3.3 Summary

At the positions Arg(20), Leu(10) and Gly(4), the mild capping mixture (2% acetic anhydride/1% DIPEA in DMF for 10 minutes) is sufficient in order to maintain the desired effect of avoiding (N−1) impurities by acylation. However, in these three cases, the respective formation of Ac(20-44) (SEQ ID NO:20), Ac(10-44)(SEQ ID NO:12) and Ac(4-44) (SEQ ID NO:6) is dependent on the capping time and also on the capping mixture. This does not apply to the position Thr(5).

EXAMPLE 5

Synthesis of Lixisenatide

The example relates to the synthesis of Lixisenatide (cf. SEQ ID NO:1). At the start of the synthesis, the solid-phase-bonded linker bears an Fmoc protecting group. The individual amino acid units were coupled starting from the C-terminus (position 44) towards the N-terminus in coupling cycles, which consist of the steps of Fmoc cleavage Coupling of the Fmoc-protected amino acid unit and Capping.

At the positions Arg(20), Glu(17), Gln(13), Leu(10) and Gly(4), the capping method according to the invention (2% acetic anhydride/1% DIPEA in DMF for 10 minutes) was used. For these positions, the instructions for a coupling cycle are described below. At the other positions, capping was carried out with 10% acetic anhydride/5% DIPEA in DMF for 20 minutes. This capping is described, by way of example, at the position Thr(5). The capping method according to the invention comprises milder conditions.

The batch size was 1050 mmol of Rink resin.

5.1. Coupling of Fmoc-Arg(Pbf)-OH at Position 20

5.1.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 30 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.1.2 Coupling of Fmoc-Arg(Pbf)-OH 21 l of DMF were added to the reactor. Thereafter, 2.125 kg of FmocArg(Pbf)-OH were weighed in and 5.3 l of DMF were added. After complete dissolution, this solution was emptied into the reactor, followed by a solution of 502 g hydroxybenzotriazole hydrate (HOBt hydrate) in 2.2 l of DMF. Finally, 413 g of N,N-diisopropylcarbodiimide (DIC) were added to the reactor. The coupling time was 6-18 h. After coupling, the solvent was filtered off from the resin by suction and the capping was immediately continued.

5.1.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.2. Coupling of Fmoc-Glu(OtBu)-OH Hydrate at Position 17

5.2.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 30 min; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.2.2 Coupling of Fmoc-Glu(OtBu)-OH Hydrate 21 l of DMF were added to the reactor. Thereafter, 1.453 kg of FmocGlu(OtBu)-OH hydrate were weighed in and 5.3 l of DMF were added. After complete dissolution, this solution was emptied into the reactor, followed by a solution of 502 g hydroxybenzotriazole hydrate (HOBt hydrate) in 2.2 l of DMF. Finally, 413 g of N,N-diisopropylcarbodiimide (DIC) were added to the reactor. The coupling time was 6-18 h. After coupling, the solvent was filtered off from the resin by suction and the capping was immediately continued.

5.2.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.3 Coupling of Fmoc-Gln(Trt)-OH at Position 13

5.3.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 35 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.3.2 Coupling of Fmoc-Gln(Trt)-OH 21 l of DMF were added to the reactor. Thereafter, 2.001 kg of FmocGln(Trt)-OH were weighed in and 5.3 l of DMF were added. After complete dissolution, this solution was emptied into the reactor, followed by a solution of 502 g of hydroxybenzotriazole hydrate (HOBt hydrate) in 2.2 l of DMF. Finally, 413 g of N,N-diisopropylcarbodiimide (DIC) were added to the reactor. The coupling time was 6-18 h. After coupling, the solvent was filtered off from the resin by suction and the capping was immediately continued.

5.3.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.4 Coupling of Fmoc-Leu-OH at Position 10

5.4.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 35 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.4.2 Coupling of Fmoc-Leu-OH 21 l of DMF were added to the reactor. Thereafter, 1.158 kg of Fmoc-Leu-OH were weighed in and 5.3 l of DMF were added. After complete dissolution, this solution was emptied into the reactor, followed by a solution of 502 g hydroxybenzotriazole hydrate (HOBt hydrate) in 2.2 l of DMF. Finally, 413 g of N,N-diisopropylcarbodiimide (DIC) were added to the reactor. The coupling time was 6-18 h. After coupling, the solvent was filtered off from the resin by suction and the capping was immediately continued.

5.4.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.5 Coupling of Fmoc-Gly-OH at Position 4

5.5.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 35 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.5.2 Coupling of Fmoc-Gly-OH 21 l of DMF were added to the reactor. Thereafter, 1.217 kg of Fmoc-Gly-OH were weighed in and 5.3 l of DMF were added. After complete dissolution, this solution was emptied into the reactor, followed by a solution of 627 g of hydroxybenzotriazole hydrate (HOBt hydrate) in 2.2 l of DMF. Finally, 517 g of N,N-diisopropylcarbodiimide (DIC) were added to the reactor. The coupling time was 6-18 h. After coupling, the solvent was filtered off from the resin by suction and the capping was immediately continued.

5.5.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.6 Coupling of Fmoc-Thr(tBu)-OH at Position 5

5.6.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 35 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.6.2 Coupling of Fmoc-Thr(tBu)-OH 21 l of DMF were added to the reactor. Thereafter, 1.628 kg of FmocThr(tBu)-OH were weighed in and 5.3 l of DMF were added. After complete dissolution, this solution was emptied into the reactor, followed by a solution of 627 g of hydroxybenzotriazole hydrate (HOBt hydrate) in 2.2 l of DMF. Finally, 517 g of N,N-diisopropylcarbodiimide (DIC) were added to the reactor. The coupling time was 6-18 h. After coupling, the solvent was filtered off from the resin by suction and the capping was immediately continued.

5.6.3 Capping

The reactor was filled with 10.5 l of DMF. At the same time, 15.8 l of DMF, 3.2 l of acetic anhydride and 1.6 l of diisopropylethylamine (DIPEA) were mixed in a mixing vessel and added to the resin in the reactor. The reactor was stirred for 20 minutes, then filtering with suction was carried out. After the capping, the resin was washed 5 times in the following sequence: DMF (24 l), isopropanol (31.1 l), DMT (8 l), DMF (31.5 l), DMF (31.5 l). The reactor here was filled each time with the respective washing solvent, then stirring was carried out for 3 minutes and filtering with suction was carried out again.

5.7 Results

The HPLC chromatogram of the crude product of the Lixisenatide synthesis with the capping method according to the invention at the positions Arg(20), Glu(17), Gln(13), Leu(10) and Gly(4), and capping in the other couplings as described under 5.6.3, is shown in FIGS. 6A-6C. The peaks with the impurities acetyl(20-44), acetyl(17-44), acetyl(13-44), acetyl(10-44) and acetyl(4-44)/acetyl(6-44) are indicated.

5.8 Comparison

The capping steps of all couplings, as described under 5.6.3, were carried out, leading to increased formation of the undesired erroneous sequences Ac(20-44)(SEQ ID NO:20), Ac(17-44)(SEQ ID NO:17), Ac(13-44)(SEQ ID NO:15), Ac(10-44)(SEQ ID NO:12) and Ac(4-44)(SEQ ID NO:6)/Ac(6-44)(SEQ ID NO:8). The HPLC chromatogram of a crude Lixisenatide from this test is shown in FIG. 6A.

FIG. 6B shows a HPLC chromatogram of crude Lixisenatide, synthesized with the capping method according to the invention at the positions Arg(20), Glu(17), Gln(13), Leu (10) and Gly(4).

FIG. 6C shows the superimposition of the HPLC chromatograms from FIGS. 6A and B. It is apparent that the synthesis of Lixisenatide using the capping method according to the invention in batch operation led to a distinct reduction in the erroneous sequences Ac(20-44)(SEQ ID NO:20), Ac(17-44)(SEQ ID NO:17), Ac(13-44)(SEQ ID NO:15), Ac(10-44)(SEQ ID NO:12) and Ac(4-44)(SEQ ID NO:6)/Ac(6-44)(SEQ ID NO:8).

By using a milder capping mixture (2% acetic anhydride/1% DIPEA in DMF for 10 minutes), it was possible to reduce the level of acetylated erroneous sequences of Ac(20-44)(SEQ ID NO:20), Ac(17-44)(SEQ ID NO:17), Ac(13-44)(SEQ ID NO:15), Ac(10-44)(SEQ ID NO:12) and Ac(4-44)(SEQ ID NO:6) in the crude product of Lixisenatide or eliminate them therefrom. Since a Lixisenatide crude product which was prepared by the capping according to the invention included the acetylated by-products Ac(17-44) (SEQ ID NO:17), Ac(13-44)(SEQ ID NO:15) and Ac(10-44)(SEQ ID NO:12) in particular in considerably reduced amounts, the purification of Lixisenatide was simplified. As a result, pooling of the fractions after the first preparative chromatography run of Lixisenatide gave more fractions which met the specification criteria and thus did not have to be discarded. This led to an improved yield.

EXAMPLE 6

Capping at 9 Specific Positions in the Synthesis of Lixisenatide

As discussed in Example 5, the use of "mild" capping conditions in the synthesis of lixisenatide at positions Arg (20), Glu(17), Gln(13), Leu(10) or/and Gly(4) could improve the profile of undesired by-products.

This Example describes the influence of capping conditions upon the formation of acetylated and non-acetylated by-products. Variations in the temperature (15° C., room temperature [20° C.-23° C.], 30° C.), capping duration and the ingredients of the capping composition were performed:

no capping, mild capping conditions: 10 min capping with 2% acetic anhydride and 1% of DIPEA (diisopropylethylamine)

"normal" capping conditions: 20 min capping with 10% acetic anhydride and 5% of DIPEA 40 min capping with 10% acetic anhydride and 5% of DIPEA Capping conditions of the present invention are the "mild conditions". These conditions were used in Example 5. These conditions were found to be advantageous.

At the 9 positions selected in this Example, acetylated sequences are obtained at capping of the (N–1) position (FIG. 7). Additionally, undesired removal of the Fmoc group at the amino acid building block may occur during the capping step. The unprotected amino group may be acetylated by the capping reagent or capping composition. In this respect, improved capping conditions may avoid the undesired cleavage of the Fmoc group.

6.1 Capping at Position 36/35, after Coupling of the Dipeptide Building Block Pro-Pro, (36-44)

Peptide Fmoc-(36-44)-AVE0010 was produced by solid phase synthesis. The resin was dried in divided into 4 portions. Each portion underwent one of the four capping procedures described above at room temperature (20° C.-23° C.). Samples were dried, and the peptide was cleaved from the resin. This procedure was repeated, wherein capping was performed at 15° C. or 30° C.

In a total 12 peptide samples were obtained. The 12 peptide samples were analyzed with LCMS. Molecular weights were determined from the TIC (total ion current). The molecular weights of the following compounds were determined:

TABLE 7

| | |
|---|---|
| Ac(36-44) (SEQ ID NO: 26) | can be formed by Fmoc cleavage during capping and subsequent acetylation (undesired by-product) |
| Fmoc(36-44) | desired product (main product) of solid phase synthesis |
| (36-44) | can be formed by Fmoc cleavage during capping, but no acetylation takes place (undesired by-product) |
| (38-44) | may be still present if coupling of the Fmoc-dipeptide building block was incomplete, but no acetylation takes place during the capping step (undesired by-product) |
| Ac(38-44) | desired capping product, may be formed by capping if coupling of the Fmoc-dipeptide building block was incomplete. |

Table 8 shows the content of products obtained after Fmoc-ProPro coupling and subsequence capping (% of total peptide content).

|  | Ac(36-44) (SEQ ID NO: 26) | Fmoc(36-44) | (36-44) | (38-44) | Ac(38-44) |
|---|---|---|---|---|---|
| Position 36/35 Pro-Pro, 15° C. | | | | | |
| without capping | 0.02 | 99.96 | 0 | 0.02 | 0 |
| 10 min, 2% Ac2O, 1% DIPEA (mild) | 0.37 | 99.6 | 0 | 0.03 | 0 |
| 20 min, 10% Ac2O, 5% DIPEA (normal) | 0.09 | 99.73 | 0 | 0.18 | 0 |
| 40 min, 10% Ac2O, 5% DIPEA | 0.4 | 99.57 | 0 | 0.02 | 0 |
| Position 36/35 Pro-Pro, RT | | | | | |
| without capping | 0.09 | 99.84 | 0 | 0 | 0.06 |
| 10 min, 2% Ac2O, 1% DIPEA (mild) | 0.47 | 99.47 | 0 | 0 | 0.06 |
| 20 min, 10% Ac2O, 5% DIPEA (normal) | 0.9 | 99.04 | 0 | 0 | 0.06 |
| 40 min, 10% Ac2O, 5% DIPEA | 1.52 | 98.42 | 0 | 0 | 0.05 |
| Position 36/35 Pro-Pro, 30° C. | | | | | |
| without capping | 0 | 100 | 0 | 0 | 0 |
| 10 min, 2% Ac2O, 1% DIPEA (mild) | 0.21 | 99.79 | 0 | 0 | 0 |
| 20 min, 10% Ac2O, 5% DIPEA (normal) | 0.66 | 99.34 | 0 | 0 | 0 |
| 40 min, 10% Ac2O, 5% DIPEA | 2.39 | 97.61 | 0 | 0 | 0 |

The results are described in FIG. 8. Compounds (36-44), (38-44) and Ac(38-44) were not found, or were found in small amounts. The amount of the undesired product Ac(36-44)(SEQ ID NO:26) increases with the strength of the capping cocktail and capping duration in most cases. The amount of this product increases with temperature.

6.2 Capping at Position 23, after Coupling of the Building Ile, (23-44)

The synthesis of Fmoc(23-44) was performed as described in section 6.1. Experiments at 15° C./30° C. and at room temperature were performed with different batches.

Table 9 shows the content of products obtained after Fmoc-Ile coupling and subsequence capping (% of total peptide content)

The results are described in FIG. 9. Depending upon the capping reagent at RT and 30° C., the content of undesired compound Ac(23-44)(SEQ ID NO:23) increases. "Normal" capping at 20° C. results in 0.26% of Ac(23-44)(SEQ ID NO:23). Prolongation of capping (40 min instead of 20 min) has a negative impact on the Ac(23-44)(SEQ ID NO:23) content.

Formation of the desired product Ac(24-44) is independent from the capping composition.

6.3 Capping at Position 21, after Coupling of the Building Block Leu, (21-44)

The synthesis of Fmoc(21-44) was performed as described in section 6.1. Experiments at 15° C./30° C. and at room temperature were performed with different batches.

|  | Ac(23-44) (SEQ ID NO: 23) | Fmoc(23-44) | (23-44) | (24-44) | Ac(24-44) |
|---|---|---|---|---|---|
| Position 23 Ile, 15° C. | | | | | |
| without capping | 0 | 99.7 | 0 | 0.16 | 0.14 |
| 10 min, 2% Ac2O, 1% DIPEA (mild) | 0 | 99.56 | 0.18 | 0.11 | 0.15 |
| 20 min, 10% Ac2O, 5% DIPEA (normal) | 0 | 99.57 | 0.2 | 0.11 | 0.13 |
| 40 min, 10% Ac2O, 5% DIPEA | 0 | 99.59 | 0.16 | 0.1 | 0.15 |
| Position 23 Ile, RT | | | | | |
| without capping | 0 | 99.81 | 0 | 0.19 | 0 |
| 10 min, 2% Ac2O, 1% DIPEA (mild) | 0.13 | 99.7 | 0 | 0.16 | 0 |
| 20 min, 10% Ac2O, 5% DIPEA (normal) | 0.26 | 99.54 | 0 | 0.2 | 0 |
| 40 min, 10% Ac2O, 5% DIPEA | 0.61 | 99.21 | 0 | 0.18 | 0 |
| Position 23 Ile, 30° C. | | | | | |
| without capping | 0 | 99.66 | 0 | 0.18 | 0.16 |
| 10 min, 2% Ac2O, 1% DIPEA (mild) | 0.1 | 99.38 | 0.19 | 0.16 | 0.17 |
| 20 min, 10% Ac2O, 5% DIPEA (normal) | 0.77 | 98.65 | 0.25 | 0.15 | 0.17 |
| 40 min, 10% Ac2O, 5% DIPEA | 1.43 | 98.15 | 0.16 | 0.12 | 0.14 |

Table 10 shows the content of products obtained after Fmoc-Leu coupling and subsequence capping (% of total peptide content)

| | Ac(21-44) (SEQ ID NO: 21) | Fmoc(21-44) | (21-44) | (22-44) | Ac(22-44) (SEQ ID NO: 22) |
|---|---|---|---|---|---|
| Position 21 Leu, 15° C. | | | | | |
| without capping | 0 | 99.91 | 0 | 0 | 0.09 |
| 10 min, 2% Ac2O, 1% DIPEA (mild) | 0.03 | 99.78 | 0.07 | 0 | 0.12 |
| 20 min, 10% Ac2O, 5% DIPEA (normal) | 0.09 | 99.74 | 0.05 | 0 | 0.12 |
| 40 min, 10% Ac2O, 5% DIPEA | 0.36 | 99.48 | 0.03 | 0 | 0.13 |
| Position 21 Leu, RT | | | | | |
| without capping | 0 | 99.77 | 0 | 0.07 | 0.16 |
| 10 min, 2% Ac2O, 1% DIPEA (mild) | 0.06 | 99.64 | 0 | 0.14 | 0.16 |
| 20 min, 10% Ac2O, 5% DIPEA (normal) | 0.2 | 99.62 | 0 | 0.04 | 0.14 |
| 40 min, 10% Ac2O, 5% DIPEA | 0.46 | 99.34 | 0 | 0.04 | 0.16 |
| Position 21 Leu, 30° C. | | | | | |
| without capping | 0 | 99.86 | 0.04 | 0 | 0.11 |
| 10 min, 2% Ac2O, 1% DIPEA (mild) | 0.1 | 99.67 | 0.11 | 0 | 0.12 |
| 20 min, 10% Ac2O, 5% DIPEA (normal) | 0.86 | 98.95 | 0.06 | 0 | 0.13 |
| 40 min, 10% Ac2O, 5% DIPEA | 2.57 | 97.22 | 0.05 | 0 | 0.16 |

The results are described in FIG. 10. The content of undesired compound Ac(21-44)(SEQ ID NO:21) is largest at "40 min, 10% Ac2O, 5% DIPEA" at 15° C., RT and 30° C. The content of compound Ac(21-44)(SEQ ID NO:21) increases with temperature.

Formation of the desired compound Ac(22-44)(SEQ ID NO:22) is independent from the capping composition. Even without capping, this compound is formed.

6.4 Capping at Position 19, after Coupling of the Building Block Val, (19-44)

The synthesis of Fmoc(19-44) was performed as described in section 6.1. Experiments at 15° C./30° C. and at room temperature were performed with different batches.

Table 11 shows the content of products obtained after Fmoc-Val coupling and subsequence capping (% of total peptide content)

| | Ac(19-44) (SEQ ID NO: 19) | Fmoc(19-44) | (19-44) | (20-44) | Ac(20-44) (SEQ ID NO: 20) |
|---|---|---|---|---|---|
| Position 19 Val, 15° C. | | | | | |
| without capping | 0 | 98.98 | 0.13 | 0.46 | 0.44 |
| 10 min, 2% Ac2O, 1% DIPEA (mild) | 0.11 | 98.79 | 0.44 | 0.25 | 0.4 |
| 20 min, 10% Ac2O, 5% DIPEA (normal) | 0.56 | 98.68 | 0.14 | 0.25 | 0.37 |
| 40 min, 10% Ac2O, 5% DIPEA | 1 | 98.17 | 0.09 | 0.23 | 0.51 |
| Position 19 Val, RT | | | | | |
| without capping | 0 | 99.61 | 0 | 0.23 | 0.16 |
| 10 min, 2% Ac2O, 1% DIPEA (mild) | 0.14 | 99.52 | 0 | 0.15 | 0.2 |
| 20 min, 10% Ac2O, 5% DIPEA (normal) | 0.43 | 99.23 | 0 | 0.17 | 0.17 |
| 40 min, 10% Ac2O, 5% DIPEA | 0.9 | 98.9 | 0 | 0 | 0.2 |
| Position 19 Val, 30° C. | | | | | |
| without capping | 0 | 99.16 | 0.08 | 0.4 | 0.36 |
| 10 min, 2% Ac2O, 1% DIPEA (mild) | 0.41 | 98.59 | 0.4 | 0.27 | 0.33 |
| 20 min, 10% Ac2O, 5% DIPEA (normal) | 2.3 | 96.89 | 0.14 | 0.22 | 0.45 |
| 40 min, 10% Ac2O, 5% DIPEA | 5.09 | 94.1 | 0.11 | 0.22 | 0.48 |

The results are described in FIG. 11. The content of compound Ac(19-44)(SEQ ID NO:19) is largest at "40 min, 10% Ac2O, 5% DIPEA" at 15° C., RT and 30° C. The content of compound Ac(19-44)(SEQ ID NO:19) increases with temperature.

Formation of the desired compound Ac(20-44)(SEQ ID NO:20) increases with the strength of the capping composition. The content of undesired (20-44) decreases with increasing strength of the capping composition.

6.5 Capping at Position 18, after Coupling of the Building Block Ala, (18-44)

The synthesis of Fmoc(18-44) was performed as described in section 6.1. Experiments at 15° C./30° C. and at room temperature were performed with different batches.

Table 12 shows the content of products obtained after Fmoc-Ala coupling and subsequence capping (% of total peptide content)

|  | Ac(18-44) (SEQ ID NO: 18) | Fmoc(18-44) | (18-44) | (19-44) | Ac(19-44) (SEQ ID NO: 19) |
|---|---|---|---|---|---|
| Position 18 Ala, 15° C. | | | | | |
| without capping | 0 | 98.77 | 0.48 | 0.33 | 0.42 |
| 10 min, 2% Ac2O, 1% DIPEA (mild) | 0.48 | 98.24 | 0.53 | 0.26 | 0.49 |
| 20 min, 10% Ac2O, 5% DIPEA (normal) | 0.76 | 98.18 | 0.27 | 0.2 | 0.59 |
| 40 min, 10% Ac2O, 5% DIPEA | 1.12 | 97.91 | 0.23 | 0.22 | 0.52 |
| Position 18 Ala, RT | | | | | |
| without capping | 0 | 99.63 | 0 | 0 | 0.37 |
| 10 min, 2% Ac2O, 1% DIPEA (mild) | 0.1 | 99.43 | 0.1 | 0 | 0.36 |
| 20 min, 10% Ac2O, 5% DIPEA (normal) | 0.77 | 98.69 | 0.18 | 0 | 0.36 |
| 40 min, 10% Ac2O, 5% DIPEA | 0.38 | 99.28 | 0 | 0 | 0.38 |
| Position 18 Ala, 30° C. | | | | | |
| without capping | 0 | 98.76 | 0.53 | 0.2 | 0.5 |
| 10 min, 2% Ac2O, 1% DIPEA (mild) | 0.92 | 98.07 | 0.32 | 0.11 | 0.58 |
| 20 min, 10% Ac2O, 5% DIPEA (normal) | 2.44 | 96.67 | 0.09 | 0.14 | 0.65 |
| 40 min, 10% Ac2O, 5% DIPEA | 6.33 | 92.73 | 0.05 | 0.14 | 0.73 |

The results are described in FIG. 12. The content of undesired compound Ac(18-44)(SEQ ID NO:18) is largest at "40 min, 10% Ac2O, 5% DIPEA" at 15° C. and 30° C. The content of compound Ac(18-44)(SEQ ID NO:18) increases with temperature increase from 15° C. to 30° C.

Formation of the desired compound Ac(19-44)(SEQ ID NO:19) increases at 15° C. and 30° C. with the strength of the capping composition.

6.6 Capping at Position 15, after Coupling of the Building Block Glu (15-44)

The synthesis of Fmoc(15-44) was performed as described in section 6.1. Experiments at 15° C./30° C. and at room temperature were performed with different batches.

Table 13 shows the content of products obtained after Fmoc-Glu coupling and subsequence capping (% of total peptide content)

|  | Ac(15-44) | Fmoc(15-44) | (15-44) | (16-44) | Ac(16-44) |
|---|---|---|---|---|---|
| Position 15 Glu, 15° C. | | | | | |
| without capping | 0 | 99.28 | 0 | 0.59 | 0.13 |
| 10 min, 2% Ac2O, 1% DIPEA (mild) | 0.05 | 99.08 | 0.15 | 0.57 | 0.15 |
| 20 min, 10% Ac2O, 5% DIPEA (normal) | 0.19 | 99.08 | 0 | 0.58 | 0.15 |
| 40 min, 10% Ac2O, 5% DIPEA | 0.39 | 98.82 | 0 | 0.63 | 0.16 |
| Position 15 Glu, RT | | | | | |
| without capping | 0 | 99.72 | 0.12 | 0 | 0.17 |
| 10 min, 2% Ac2O, 1% DIPEA (mild) | 0.1 | 99.4 | 0.36 | 0 | 0.16 |
| 20 min, 10% Ac2O, 5% DIPEA (normal) | 0.42 | 99.13 | 0.2 | 0.04 | 0.21 |
| 40 min, 10% Ac2O, 5% DIPEA | 0.89 | 98.65 | 0.22 | 0.05 | 0.19 |
| Position 15 Glu, 30° C. | | | | | |
| without capping | 0 | 98.93 | 0 | 0.91 | 0.16 |
| 10 min, 2% Ac2O, 1% DIPEA (mild) | 0.17 | 98.7 | 0 | 0.95 | 0.18 |

-continued

| | Ac(15-44) | Fmoc(15-44) | (15-44) | (16-44) | Ac(16-44) |
|---|---|---|---|---|---|
| 20 min, 10% Ac2O, 5% DIPEA (normal) | 1.62 | 97.3 | 0 | 0.88 | 0.2 |
| 40 min, 10% Ac2O, 5% DIPEA | 3.24 | 95.63 | 0 | 0.94 | 0.19 |

The results are described in FIG. 13. The content of undesired compound Ac(15-44) is largest at "40 min, 10% Ac2O, 5% DIPEA" at 15° C., RT and 30° C. The content of compound Ac(15-44) increases with temperature.

Formation of the desired compound Ac(16-44) is independent from the capping composition. Even without capping, this compound is formed.

6.7 Capping at Position 12, after Coupling of the Building Block Lys (12-44)

The synthesis of Fmoc(12-44) was performed as described in section 6.1. Experiments at 15° C./30° C. and at room temperature were performed with different batches.

Table 14 shows the content of products obtained after Fmoc-Lys coupling and subsequence capping (% of total peptide content)

| | Ac(12-44) (SEQ ID NO: 14) | Fmoc(12-44) | (12-44) | (13-44) | Ac(13-44) (SEQ ID NO: 15) |
|---|---|---|---|---|---|
| Position 12 Lys, 15° C. | | | | | |
| without capping | 0 | 99.43 | 0.13 | 0 | 0.44 |
| 10 min, 2% Ac2O, 1% DIPEA (mild) | 0.15 | 99.25 | 0.17 | 0 | 0.43 |
| 20 min, 10% Ac2O, 5% DIPEA (normal) | 0.3 | 99.03 | 0.17 | 0 | 0.49 |
| 40 min, 10% Ac2O, 5% DIPEA | 0.55 | 98.88 | 0.16 | 0 | 0.41 |
| Position 12 Lys, RT | | | | | |
| without capping | 0 | 99.12 | 0 | 0.17 | 0.71 |
| 10 min, 2% Ac2O, 1% DIPEA (mild) | 0 | 99.29 | 0 | 0 | 0.71 |
| 20 min, 10% Ac2O, 5% DIPEA (normal) | 0.5 | 98.76 | 0 | 0 | 0.74 |
| 40 min, 10% Ac2O, 5% DIPEA | 1.12 | 98.15 | 0 | 0 | 0.73 |
| Position 12 Lys, 30° C. | | | | | |
| without capping | 0 | 99.41 | 0.15 | 0 | 0.44 |
| 10 min, 2% Ac2O, 1% DIPEA (mild) | 0.35 | 99.02 | 0.16 | 0 | 0.47 |
| 20 min, 10% Ac2O, 5% DIPEA (normal) | 1.55 | 97.89 | 0.14 | 0 | 0.41 |
| 40 min, 10% Ac2O, 5% DIPEA | 3.53 | 95.87 | 0.16 | 0 | 0.44 |

The results are described in FIG. 14. The content of undesired compound Ac(12-44)(SEQ ID NO:14) is largest at "40 min, 10% Ac2O, 5% DIPEA" at 15° C., RT and 30° C. The content of compound Ac(12-44)(SEQ ID NO:14) increases with temperature.

Formation of the desired compound Ac(13-44)(SEQ ID NO:15) is independent from the capping composition. Even without capping, this compound is formed.

6.8 Capping at Position 8, after Coupling of the Building Block Ser (8-44)

The synthesis of Fmoc(8-44) was performed as described in section 6.1. Experiments at 15° C., RT and 30° C. were performed with the same batch.

Table 15 shows the content of products obtained after Fmoc-Ser coupling and subsequence capping (% of total peptide content)

| | Ac(8-44) (SEQ ID NO: 10) | Fmoc(8-44) | (8-44) | (9-44) | Ac(9-44) (SEQ ID NO: 11) |
|---|---|---|---|---|---|
| Position 8 Ser, 15° C. | | | | | |
| without capping | 0 | 100 | 0 | 0 | 0 |
| 10 min, 2% Ac2O, 1% DIPEA (mild) | 0 | 99.79 | 0 | 0 | 0.21 |
| 20 min, 10% Ac2O, 5% DIPEA (normal) | 0.29 | 99.53 | 0 | 0 | 0.18 |
| 40 min, 10% Ac2O, 5% DIPEA | 1.08 | 98.72 | 0 | 0 | 0.21 |

-continued

|  | Ac(8-44) (SEQ ID NO: 10) | Fmoc(8-44) | (8-44) | (9-44) | Ac(9-44) (SEQ ID NO: 11) |
|---|---|---|---|---|---|
| Position 8 Ser, RT | | | | | |
| without capping | 0 | 99.67 | 0 | 0.18 | 0.16 |
| 10 min, 2% Ac2O, 1% DIPEA (mild) | 0.22 | 99.78 | 0 | 0 | 0 |
| 20 min, 10% Ac2O, 5% DIPEA (normal) | 1.12 | 98.88 | 0 | 0 | 0 |
| 40 min, 10% Ac2O, 5% DIPEA | 2.1 | 97.9 | 0 | 0 | 0 |
| Position 8 Ser, 30° C. | | | | | |
| without capping | 0 | 100 | 0 | 0 | 0 |
| 10 min, 2% Ac2O, 1% DIPEA (mild) | 0.29 | 99.27 | 0.27 | 0 | 0.18 |
| 20 min, 10% Ac2O, 5% DIPEA (normal) | 2.1 | 97.8 | 0 | 0 | 0.1 |
| 40 min, 10% Ac2O, 5% DIPEA | 5.02 | 94.74 | 0 | 0 | 0.24 |

The results are described in FIG. 15. The content of undesired compound Ac(8-44)(SEQ ID NO:10) is largest at "40 min, 10% Ac2O, 5% DIPEA" at 15° C., RT and 30° C. The content of compound Ac(8-44)(SEQ ID NO:10) increases with temperature.

6.9 Capping at Position 6, after Coupling of the Building Block Phe (6-44)

The synthesis of Fmoc(86-44) was performed as described in section 6.1. Experiments at 15° C., RT and 30° C. were performed with the same batch.

Table 16 shows the content of products obtained after Fmoc-Phe coupling and subsequence capping (% of total peptide content)

|  | Ac(6-44) (SEQ ID NO: 8) | Fmoc(6-44) | (6-44) | (7-44) | Ac(7-44) (SEQ ID NO: 9) |
|---|---|---|---|---|---|
| Position 6 Phe, 15° C. | | | | | |
| without capping | 0 | 99.21 | 0 | 0.38 | 0.41 |
| 10 min, 2% Ac2O, 1% DIPEA (mild) | 0 | 99 | 0.39 | 0.28 | 0.34 |
| 20 min, 10% Ac2O, 5% DIPEA (normal) | 0.35 | 98.73 | 0.32 | 0.26 | 0.33 |
| 40 min, 10% Ac2O, 5% DIPEA | 0.62 | 98.6 | 0.3 | 0.18 | 0.3 |
| Position 6 Phe, RT | | | | | |
| without capping | 0 | 99.24 | 0 | 0.39 | 0.37 |
| 10 min, 2% Ac2O, 1% DIPEA (mild) | 0.2 | 98.68 | 0.6 | 0.25 | 0.28 |
| 20 min, 10% Ac2O, 5% DIPEA (normal) | 0.57 | 98.49 | 0.31 | 0.25 | 0.38 |
| 40 min, 10% Ac2O, 5% DIPEA | 1.32 | 97.9 | 0.33 | 0.2 | 0.24 |
| Position 6 Phe, 30° C. | | | | | |
| without capping | 0 | 99.24 | 0 | 0.43 | 0.33 |
| 10 min, 2% Ac2O, 1% DIPEA (mild) | 0.33 | 98.36 | 0.55 | 0.29 | 0.46 |
| 20 min, 10% Ac2O, 5% DIPEA (normal) | 1.54 | 97.42 | 0.37 | 0.3 | 0.37 |
| 40 min, 10% Ac2O, 5% DIPEA | 3.73 | 95.91 | 0 | 0 | 0.36 |

The results are described in FIG. 16. The content of undesired compound Ac(6-44)(SEQ ID NO:8) is largest at "40 min, 10% Ac2O, 5% DIPEA" at 15° C., RT and 30° C. The content of compound Ac(6-44)(SEQ ID NO:8) increases with temperature.

Formation of the desired compound Ac(7-44)(SEQ ID NO:9) is independent from the capping composition. Even without capping, this compound is formed.

Temperature has only slight influence on formation of the desired compound Ac(7-44)(SEQ ID NO:9). The content of undesired (7-44) decreases with increasing strength of the capping composition.

6.10 Summary

Undesired formation of Ac(X-44)-compound strongly depends upon the capping duration, the capping composition and the capping temperature. With increasing capping duration, increasing capping temperature, and increased content of acetic anhydride and DIPEA in the capping composition the content of undesired Ac(X-44) compound increases.

6.1 1 Capping Under "Normal" Conditions, Depending Upon Temperature.

FIGS. 17 and 18 summarize the data obtained in capping at different temperatures at the 9 positions in the synthesis of Lixisenatide under "normal" conditions "20 min, 10% Ac2O, 5% DIPEA", as described in this Example.

FIG. 17 shows a comparison of GMP capping of Ac(X-44), depending on reaction temperature. Values given for 15° C. and 30° C. are positive and negative deviations from "room temperature" values (grey area).

The formation of undesired product Ac(X-44) is 0.5% in 5 of 9 positions, in 3 positions between 0.5% and 1%, and in only one position >1%. A large increase is observed at 30° C., while at 15° C., formation of Ac(X-44) slightly decreases.

This means that GMP capping "20 min, 10% Ac2O, 5% DIPEA" can be performed at different positions between 15° C. and room temperature, which can be 20-23° C.

FIG. 18 shows a comparison of GMP capping of Ac[(X-1)-44], depending on reaction temperature. Values given for 15° C. and 30° C. are positive and negative deviations from "room temperature" values (grey area)

Regarding the desired formation of the Ac[(X-1)-44] compounds at RT, the deviation at 15° C. is between +0.23 und −0.25%. At 30° C., the deviation is between +0.29 und −0.33%. Formation of the desired capping product Ac[(X-1)-44] is thus less dependent upon the temperature than the undesired formation of Ac(X-44).

At 15° C. and 30° C., negative deviations of the content of desired compound Ac[(X-1)-44] are observed in view of capping at room temperature. This means that capping with "normal" conditions should be performed at room temperature.

6.12 Capping with Different Capping Compositions at Room Temperature.

FIGS. 19 and 20 summarize the data obtained in capping with different capping compositions at room temperature at the 9 positions in the synthesis of lixisenatide, as described in this Example.

FIG. 19 shows a comparison of Ac(X-44) content, depending upon the capping composition at room temperature. Values given for "no capping", "mild" and "40 min" conditions are positive and negative deviations from "normal capping" values (grey area).

Formation of undesired product Ac(X-44) under "20 min, 10% Ac2O, 5% DIPEA" and "40 min, 10% Ac2O, 5% DIPEA" is largest. Formation of Ac(X-44) under "normal" conditions (40 min, 10% Ac2O, 5% DIPEA) is between 0.2% and 1.12%. A strong decrease is observed at mild capping conditions.

FIG. 20 shows a comparison of Ac[(X-1)-44] content, depending upon the capping composition at room temperature. Values given for "no capping", "mild" and "40 min" are positive and negative deviations from "normal capping" values (grey area).

The formation of the desired product Ac[(X-1)-44] at the conditions "no capping", "mild" and "40 min" is within −0.14% and +0.16% in view of the "normal" conditions.

In particular, under "mild" conditions (10 min, 2% Ac2O, 1% DIPEA) of the invention, sufficient capping can be achieved in the synthesis of lixisenatide.

In summary, mild capping conditions, in particular capping for 10 min with 2% Ac2O and 1% DIPEA in a solvent, are advantageous in the solid phase synthesis of lixisenatide, as described herein.

If capping is omitted after coupling at certain amino acid positions, undesired by-products comprising an incomplete amino acid sequence and being present in small amount, may be difficult to remove during the purification process.

EXAMPLE 7

Cleavage of Lixisenatide from the Solid Phase

This example relates to the cleavage according to the invention of Lixisenatide from a solid phase. A solid phase (Rink resin) was provided, to which the peptide Lixisenatide was bonded. The peptide was synthesized on the resin by stepwise coupling of amino acid units.

As comparative test, a cleavage according to the prior art (King et al., Int. J. Peptide Protein Res. 1990, 36: 255-266) was carried out.

The cleavage method according to the invention is distinguished from the method of the prior art by the following changes:

Reaction temperature from 20° C. to 26° C.

Number of components in the cleavage mixture reduced from 5 to 2 constituents, combined with increase in the ratio of resin to cleavage mixture used.

TABLE 17

Comparison of the cleavage method according to the invention and the cleavage according to the prior art. The differences are indicated in bold/underlined.

| Comparative process (prior art) | Method according to the invention |
|---|---|
| Cleavage mixture [g or ml/g "peptide on resin"]: a) 0.5 g phenol b) 0.5 ml thioanisole c) 0.25 ml 1,2-ethanedithiol d) 0.5 ml water e) 8.25 ml TFA ("King's cocktail") | Cleavage mixture [ml/g "peptide on resin"]: a) 0.25 ml 1,2-ethanedithiol b) 8.25 ml TFA |
| Cleavage mixture is cooled to 5-10° C. and added to Lixisenatide-resin(1-44) (SEQ ID NO: 1) | Cleavage mixture is cooled to 5-10° C. and added to Lixisenatide-resin(1-44) (SEQ ID NO: 1) |
| Reaction mixture heated to 20° C. and stirred for 4 h | Reaction mixture heated to 26° C. and stirred for 4 h |
| Reaction mixture filtered | Reaction mixture filtered |
| Subsequent cleavage | Subsequent cleavage |
| The resin filtered off is added to TFA (10 ml per g of resin), stirred for 1 h and the resin is filtered off | The resin filtered off is added to TFA (10 ml per g of resin), stirred for 1 h and the resin is filtered off |
| Filtrate purified and solution concentrated by distillation under reduced pressure at 35-40° C. to at least 1/16th of the original volume. | Filtrate purified and solution concentrated by distillation under reduced pressure at 35-40° C. to at least 1/16th of the original volume. |

TABLE 17-continued

Comparison of the cleavage method according to the invention and the cleavage according to the prior art. The differences are indicated in bold/underlined.

| Comparative process (prior art) | Method according to the invention |
|---|---|
| Crude Lixisenatide precipitated by addition of the concentrate to 6 times the volume of DIPE | Crude Lixisenatide precipitated by addition of the concentrate to 6 times the volume of DIPE |
| The precipitate is resuspended twice in ethyl acetate and filtered off. | The precipitate is resuspended twice in ethyl acetate and filtered off. |
| The precipitate is dried and the crude Lixisenatide is isolated. | The precipitate is dried and the crude Lixisenatide is isolated. |

By using the cleavage according to the invention, compared to the cleavage according to the prior art, it was possible to increase the yields of the crude Lixisenatide by approximately 5% (from 20% to 25%), while the impurities profile was only slightly altered.

The method of this example is suitable for scale-up to the pilot-plant and production scale.

Table 18 summarizes the results obtained in the comparative process (see Table 17). Three different batches 2E002, 26008 and 26006 of lixisenatide-resin (1-44)(SEQ ID NO:1) were used. Means and standard deviation are calculated for each batch separately. Comparison between different cleavage conditions should be made in tests using the same batch of lixisenatide-resin (1-44)(SEQ ID NO:1). In different batches, the solid phase synthesis may have an impact on the yield. If not otherwise indicated, 10 g of lixisenatide-resin (1-44)(SEQ ID NO:1) were used as starting material.

TABLE 18

Content of lixisenatide in the resin, and yield of lixisenatide after cleavage of lixisenatide from the resin under standard conditions (comparative process, see Table 17).

| Number of experiment | Batch of lixisenatide-resin(1-44) (SEQ ID NO: 1) | Output weight [g] | Content [%] | Yield [%] |
|---|---|---|---|---|
| Batch 2E002 | | | | |
| 71002-002 | 2E002 | 2.60 | 22.9 | 10.2 |
| 71002-003 | 2E002 | 3.36 | 23.1 | 13.4 |
| 71002-012 | 2E002 | 1.88 | 20.3 | 6.6 |
| separate subsequent cleavage | | 0.77 | 25.0 | 3.3 |
| 70609-068 | 2E002 | 3.01 | 21.5 | 11.1 |
| 71002-035 | 2E002 | 3.08 | 16.3 | 8.6 |
| 71002-036 | 2E002 | 3.07 | 16.3 | 8.6 |
| 70586-043 | 2E002 | 2.40 | 24.3 | 10.1 |
| 71003-003 | 2E002 | 2.50 | 24.0 | 10.3 |
| Mean ± standard deviation | | | | 10.3 ± 1.5 |
| Batch 2B008 | | | | |
| 70586-052 | 2B008 | 2.84 | 26.9 | 14.7 |
| 71001-006 | 2B008 | 3.03 | 20.0 | 11.7 |
| 71002-048 | 2B008 | 2.89 | 22.8 | 12.7 |
| 71001-016 | 2B008 | 3.41 | 21.6 | 14.2 |
| Mean ± standard deviation | | | | 13.4 ± 1.4 |
| Batch 2B006 | | | | |
| 70586-056 | 2B006 | 3.02 | 25.0 | 14.3 |

7.1 Cleavage Yield Depending Upon the Cleavage Temperature Between 20° C. and 35° C.

Cleavage from the lixisenatide-resin(1-44)(SEQ ID NO:1) was performed under standard conditions (comparative process, see Table 17) for 4 h.

TABLE 19

Cleavage yield depending upon temperature

| Number of experiment | Batch of lixisenatide-resin(1-44) (SEQ ID NO: 1) | Temperature [° C.] | Duration [h] | Yield [%] |
|---|---|---|---|---|
| Standard | 2E002 | 20 | 4 | 10.3 ± 1.5 |
| 70586-050 | 2E002 | 23 | 4 | 11.7 |
| 70586-044 | 2E002 | 26 | 4 | 14.8 |
| 70586-046 | 2E002 | 30 | 4 | 14.2 |
| 70586-049 | 2E002 | 35 | 4 | 12.4 |

Results: The yield of lixisenatide after cleavage under standard conditions increases with increasing temperature until the optimum of about 26° C. Surprisingly, an increase of temperature from 23° C. to 26° C. results in a significant increase in yield.

7.2 Cleavage Yield Depending Upon the Cleavage Duration

Cleavage from the lixisenatide-resin(1-44)(SEQ ID NO:1) was performed under standard conditions (comparative process, see Table 17) at 20° C.

TABLE 20

Cleavage yield depending upon the cleavage duration

| Number of experiment | Batch of lixisenatide-resin(1-44) (SEQ ID NO: 1) | Temperature [° C.] | Duration [h] | Yield [%] |
|---|---|---|---|---|
| Standard | 2E002 | 20 | 4 | 10.3 ± 1.5 |
| 71002-037 | 2E002 | 20 | 6 | 11.3 |
| 71002-038 | 2E002 | 20 | 8 | 13.4 |
| 70586-037, 71003-002, 71003-004 | 2E002 | 20 | 12 | 13.1 ± 0.9 |

Results: The yield of lixisenatide increases with increased cleavage duration. A maximum yield is reached after about 8 h cleavage.

7.3 Cleavage Yield Depending Upon the Temperature at Cleavage Duration of 12 h

Cleavage from the lixisenatide-resin(1-44)(SEQ ID NO:1) was performed under standard conditions (comparative process, see Table 17) for 4 h.

TABLE 21

Cleavage yield depending upon the temperature at cleavage duration of 12 h

| Number of experiment | Batch of lixisenatide-resin(1-44) (SEQ ID NO: 1) | Temperature [° C.] | Duration [h] | Yield [%] |
|---|---|---|---|---|
| 70586-040 | 2E002 | 17 | 12 | 10.7 |
| 70586-037 | 2E002 | 20 | 12 | 14.1 |
| 70586-039 | 2E002 | 23 | 12 | 13.0 |
| 70586-045 | 2E002 | 26 | 12 | 14.0 |
| 70586-047 | 2E002 | 30 | 12 | 12.1 |

Results: The yield increases at a cleavage duration of 12 h if reaction temperature is increased. A maximum yield is obtained at 26° C., as described in Example 7.1 for 4 h cleavage. Tests 70586-044 (4 h, 26° C., Example 7) and 70586-045 (12 h, 26° C.) resulted in similar yields (14.8% vs. 14.0%).

7.4 Cleavage Yield Depending Upon the Cleavage Temperature Up to 20° C.

Cleavage from the lixisenatide-resin(1-44)(SEQ ID NO:1) was performed under standard conditions (comparative process, see Table 17) for 4 h.

TABLE 22

Cleavage yield depending upon the cleavage temperature up to 20° C.

| Number of experiment | Batch of lixisenatide-resin(1-44) (SEQ ID NO: 1) | Temperature [° C.] | Duration [h] | Yield [%] |
|---|---|---|---|---|
| 71002-028 | 2E002 | 0-5° C. | 21.5 | 6.0 |
| 71002-029 | 2E002 | 8-13° C. | 28 | 8.7 |
| 71002-030 | 2E002 | 8-13° C. | 40.8 | 11.2 |
| 70586-040 | 2E002 | 17° C. | 12 | 10.7 |
| Standard | 2E002 | 20° C. | 4 | 10.3 ± 1.5 |
| 70586-037, 71003-002, 71003-004 | 2E002 | 20° C. | 12 | 13.1 ± 0.9 |

Results: The cleavage at a temperature below 20° C. requires longer cleavage durations, as expected, to reach the yield obtained by cleavage at 20° C. for 4 h (standard conditions, comparative process, Table 17).

7.5 Modified Cleavage Cocktail

The standard process uses a cleavage cocktail containing five components: phenol, thioanisole, 1,2-ethandithiole, water and TFA. Subject of the example are simplified cleavage cocktails, omitting one to three of thioanisole, phenol and water. The yield of lixisenatide cleavage from lixisenatide-resin(1-44)(SEQ ID NO:1) is determined. The "no modification" cocktail is described in Table 17, "Comparative process".

TABLE 23

Modified cleavage cocktail

| Number of experiment | Batch of lixisenatide-resin(1-44) (SEQ ID NO: 1) | Modification of cleavage composition | Yield [%] |
|---|---|---|---|
| Standard | 2E002 | no modification | 10.3 ± 1.5 |
| 71002-010 | 2E002 | without thioanisole | 10.7 |
| 71002-009 | 2E002 | without phenol | 12.1 |
| 71002-006 | 2E002 | without water | 13.2 |
| 71002-008 | 2E002 | without phenol and water | 13.3 |
| 71003-008 | 2E002 | water content is reduced to 2.5% w/w | 13.3 |
| 71002-042 | 2E002 | without thioanisole, phenol and water, i.e. only TFA and 1,2-ethanedithiol | 12.7 |

Results: Omission of one or more components results in an increased yield, except test 71002-010 (omission of thioanisole).

A simplified cleavage mixture (cleavage cocktail) has several advantages:
(a) simplification of analytics and quality control,
(b) reduced costs,
(c) facilitated handling in the production process.

7.6 TFA and 1,2-Ethanedithiol Content in the Cleavage Cocktail

Starting from test 71002-042, the influence of the TFA:1,2-ethaneditihiol ratio upon cleavage yield was investigated:

TABLE 24

Different TFA and 1,2-ethanedithiol ratio in the cleavage cocktail

| Number of Experiment | Batch of Lixisenatide-resin (1-44) (SEQ ID NO: 1) | Volume in mL of TFA and 1,2-ethanedithiol per g „peptide on resin" | Yield [%] |
|---|---|---|---|
| Standard | 2E002 | | 10.3 ± 1.5 |
| 71002-045 | 2E002 | 8:2 | 6.5 |
| 71002-043 | 2E002 | 9:1 | 9.3 |
| 71002-044 | 2E002 | 9:0.5 | 11.0 |
| 71002-042 | 2E002 | 8.25:0.25 | 12.7 |
| Standard | 2B008 | | 13.4 ± 1.4 |
| 71002-046 | 2B008 | 8.25:0.25 | 15.6 |
| 71002-047 | 2B008 | 8.25:0.25 | 14.3 |

Results: An increase in the 1,2-ethanedithiol content results in a significant decrease of lixisenatide yield. The TFA:1,2-ethanedithiol ratio of 8.25:0.25 was found to be the ratio with largest yield (batch 2E002). This finding was confirmed by to experiments using batch 2B008.

7.7 Volume of the Cleavage Cocktail

The influence of volume (and thus concentration) of the cleavage cocktail was investigated

TABLE 25

Cleavage yield, depending upon volume of the cleavage cocktail.

| Number of Experiment | Batch of Lixisenatide-resin (1-44) (SEQ ID NO: 1) | Reduction of volume [%] | Yield [%] |
|---|---|---|---|
| Standard | 2E002 | 0% | 10.3 ± 1.5 |
| 71002-026 | 2E002 | −10% | 13.3 |
| 71002-040 | 2E002 | −15% | 10.3 |
| 71002-025 | 2E002 | −25% | 11.0 |
| 70609-069 | 2E002 | −30% | 10.5 |
| 71002-031 | 2E002 | −50% | 7.9 |

Results: The reduction of up to 30% has no influence upon cleavage yield. Larger volume reductions lead to a decreased yield.

7.8 Swelling of the "Peptide on Resin" with a Co-Solvent (Toluol or $CH_2Cl_2$) Before Cleavage The rationale behind this experiment is the finding that cleavage of lixisenatide from the resin may result in an increase in temperature of up to 5-8° C., which may lead to formation of undesired by-products and potentially has a negative impact upon stability and thus the cleavage yield. Swelling of the "peptide on resin" in an organic solvent may reduce the exotherm and thus may increase the yield.

TABLE 26

Cleavage yield, depending upon the presence of a co-solvent.

| Number of Experiment | Batch of Lixisenatide-resin (1-44) (SEQ ID NO: 1) | Swelling with organic solvent | Duration [h] | Increase of temperature [° C.] | Yield [%] |
|---|---|---|---|---|---|
| Standard | 2E002 | without | | 5-8° C. | 10.3 ± 1.5 |
| 71002-016 | 2E002 | 30 ml toluol* | 4 h | 1-2° C. | 9.8 |
| 71002-019 | 2E002 | 30 ml toluol | 6 h | 1-2° C. | 6.1 |
| 71002-021 | 2E002 | 30 ml toluol | 17 h | 1-2° C. | 9.3 |
| 71002-017 | 2E002 | 50 ml toluol | 28 h | 1-2° C. | 4.7 |
| 71002-024 | 2E002 | 30 ml $CH_2Cl_2$ | 24 h | 1-2° C. | 7.3 |

*The total volume of TFA and toluol/$CH_2Cl_2$ is kept constant.

Results: Swelling with an organic co-solvent does not increase the cleavage yield.

7.9 Concentration in the Presence of a Co-Solvent

The presence of a co-solvent, having a higher boiling point than TFA, and in which lixisenatide is insoluble, may increase the yield after cleavage from the resin, because during distillation of TFA from the filtrate, the presence of the co-solvent may lead to precipitation of lixisenatide, and therefore can prevent the degradation of lixisenatide during cleavage in King's cocktail.

TABLE 27

Cleavage yield, depending upon the presence of a co-solvent during TFA distillation.

| Number of Experiment | Batch of lixisenatide-resin(1-44) (SEQ ID NO: 1) | Solvent | Yield [%] |
|---|---|---|---|
| Standard | 2E002 | Ohne | 10.3 ± 1.5 |
| 71002-004 | 2E002 | Toluol | 12.0 |
| 71002-014 | 2E002 | n-Heptan | 11.1 |

Results: The presence of toluol in the distillation of the filtrate after cleavage of lixisenatide from the resin leads to a slightly increased yield.

7.10 Optimized Cleavage Procedure of the Invention

Based upon the above-described results obtained in this Example, optimized cleavage conditions as follows were selected and tested:

(a) reaction temperature of 26° C., (b) cleavage cocktail consists of TFA and 1,2-ethanedithiol. The cocktail contained about 97% of TFA and about 3% of 1,2-ethanedithiol. An amount of 8.25 ml/g "peptide on resin" of TFA and 0.25 ml/g "peptide on resin" of 1,2-ethanedithiol was used.

The cleavage yield of this cocktail, compared with the standard comparative cocktail, was tested in batches 2E002 and 26008.

TABLE 28

Optimized cleavage procedure of the invention

| Number of experiment | Batch of Lixisenatide-resin (1-44) (SEQ ID NO: 1) | Modification of cleavage composition | Yield [%] |
|---|---|---|---|
| Standard | 2E002 | no modification | 10.3 ± 1.5 |
| 70586-051 | 2E002 | 26° C., only TFA and EDT | 14.9 |
| 71001-012 | 2E002 | 26° C., only TFA and EDT | 15.8 |

TABLE 28-continued

Optimized cleavage procedure of the invention

| Number of experiment | Batch of Lixisenatide-resin (1-44) (SEQ ID NO: 1) | Modification of cleavage composition | Yield [%] |
|---|---|---|---|
| Mean ± standard deviation | | | 15.4 ± 0.6 |
| Standard | 2B008 | no modification | 13.4 ± 1.4 |
| 70586-051 | 2B008 | 26° C., only TFA and EDT | 18.5 |
| 71001-013 | 2B008 | 26° C., only TFA and EDT | 19.7 |
| Mean ± standard deviation | | | 19.4 ± 0.4 |

Results: In both batches, the yield increased by about 5%, indicating a significant improvement of the peptide cleavage from the solid phase by the method of the invention.

7.11 Second (Subsequent) Cleavage

After the cleavage, using the comparative cocktail (King's cocktail) or the cleavage cocktail of the invention, a second (subsequent) cleavage, was performed (see Table 17).

The first cleavage was performed, a filtrate was obtained. TFA was added to the TFA-wet resin. After 1 h stirring, the resin was filtrated. The filtrates were combined and concentrated.

The effect of the second, subsequent cleavage upon lixisenatide yield was investigated.

TABLE 29

Influence of a second (subsequent) cleavage of lixisenatide yield.

| Number of experiment | Batch of Lixisenatide-resin (1-44) (SEQ ID NO: 1) | Modification of cleavage composition | Subsequent cleavage (TFA only) | Yield [%] |
|---|---|---|---|---|
| Standard | 2B008 | 26° C., only TFA and EDT | yes | 13.4 ± 1.4 |
| 70586-051 | 2B008 | 26° C., only TFA and EDT | yes | 18.5 |
| 71001-013 | 2B008 | 26° C., only TFA and EDT | yes | 19.7 |
| Mean ± standard deviation | | | | 19.1 ± 0.4 |
| 70001-018 | 2B008 | 26° C., only TFA and EDT | no | 17.9 |
| 70001-019 | 2B008 | 26° C., only TFA and EDT | no | 18.1 |
| 70609-078 | 2B008 | 26° C., only TFA and EDT | no | 18.1 |
| 70001-020 | 2B008 | 26° C., only TFA and EDT | no | 20.1 |
| Mean ± standard deviation | | | | 18.4 ± 1.1 |

EDT: 1.2-ethanedithiol.

Results: Subsequent cleavage results in an increase of the yield of only about 0.7%. This increase is associated with a significant increase in costs for starting materials (TFA), and additional efforts to remove the TFA from the peptide preparation. It must be considered that by combination of the filtrates of the first and second cleavage step, the amount of TFA significantly increases.

It is concluded that in view of the small increase in yield, omission of the second cleavage leads to a cost reduction, and handling during the production process is facilitated. The amounts of TFA are reduced, so that removal of TFA is facilitated.

7.12 Analytics

Two batches, 71001-016 (comparative batch, cleavage with King's cocktail according to the standard method), and 71001-013 (lixisenatide cleavage according to the invention) were prepared.

TABLE 30 analytics

| | Output weight [g] | Content against external standard [%] | Purity [Fl.-%] | Yield [%] |
|---|---|---|---|---|
| 71001-016 (comparative) | 3.41 | 23.0 | 35.6 | 14.2 |
| 71001-013 (invention) | 5.20 | 20.5 | 35.9 | 19.7 |

Results: The batches showed almost identical purity. The content in the batch produced according to the invention is slightly decreased. In the batch of the invention, the output weight is increased, resulting in an increased yield.

7.13 Summary

The cleavage method of the invention has the following advantages:
(a) increase of lixisenatide yield by about 5%, resulting in a cost reduction and an increase of production capacity.
(b) only two components are present in the cleavage cocktail (in view of five components in the comparative King's cocktail), thus analytic quality control is improved and costs are reduced,
(c) omission of the second cleavage leads to a cost reduction, and handling during the production process is facilitated. The amounts of TFA are reduced, so that removal of TFA is facilitated.

The following aspects are also subject of the invention:
1. A method for the synthesis of a polypeptide comprising a pre-determined amino acid sequence, the method comprising coupling cycles of amino acid building blocks to an amino acid chain,
    wherein said amino acid building blocks comprise an unprotected C-terminal carboxyl group and a protected N-terminal amino group, and wherein said amino acid chain comprises an unprotected N-terminal amino group,
    wherein at least one coupling cycle comprises the steps:
    (a) coupling the amino acid building block C-terminally at the unprotected N-terminal amino group of the amino acid chain, so that an amide bond is formed between the amino acid chain and the amino acid building block,
    (b) contacting the product obtained in step (a) with a capping reagent comprising a capping compound, wherein the capping compound binds to an unprotected N-terminal amino group of the amino acid chain to which no building block has been coupled in step (a), and
    (c) de-protecting the N-terminal amino group of the amino acid building block.
2. The method of item 1, wherein the capping compound is selected from the group consisting of acetic anhydride (CAS 108-24-7), homologues of acetic anhydride, benzoyl chloride (CAS 98-88-4), N-(benzyloxycarbonyloxy)

succinimide (CAS 13139-17-8), benzyl chloroformate (CAS 501-53-1), esters of chloroformic acid, 1-acetylimidazole (CAS 2466-76-4), di-tert-butyl dicarbonate (CAS 24424-99-5) and N-(tert-butoxycarbonyloxy)succinimide (CAS 13139-12-3).
3. The method of item 1 or 2, wherein the capping reagent comprises 0.5-5% v/v of acetic anhydride.
4. The method of any one of the preceding items, wherein the capping reagent comprises 1-3% v/v of acetic anhydride.
5. The method of any one of the preceding items, wherein the capping reagent comprises 2% v/v of acetic anhydride.
6. The method of any one of the preceding items, wherein the capping reagent comprises 0.2-2% v/v of diisopropylethylamine.
7. The method of any one of the preceding items, wherein the capping reagent comprises 0.5-2% v/v of diisopropylethylamine.
8. The method of any one of the preceding items, wherein the capping reagent comprises 1% v/v of diisopropylethylamine.
9. The method of any one of the preceding items, wherein the capping reagent comprises 1% v/v of diisopropylethylamine and 2% v/v of acetic anhydride.
10. The method of any one of the preceding items, wherein the capping reagent comprises DMF.
11. The method of any one of the preceding items, wherein the step (b) is performed at a temperature of 15-25° C.
12. The method of any one of the preceding items, wherein the step (b) is performed for 5 to 15 min.
13. The method of any one of the preceding items, wherein the amino acid building block comprises an α-amino acid.
14. The method of any one of the preceding items, wherein the amino acid building block is selected from Ser, Thr, Trp, Lys, Ala, Asn, Asp, Val, Met, Phe, Ile, Pro, Arg, Glu, Gln, Leu and Gly.
15. The method of any one of the preceding items, wherein the amino acid building block is selected from Arg, Glu, Gln, Leu and Gly.
16. The method of any one of the preceding items, wherein the side chain of the amino acid building block comprises a protecting group which is orthogonal to the N-terminal protecting group of the amino acid building block.
17. The method of any one of the preceding items, comprising a solid phase synthesis.
18. The method of any one of the preceding items, wherein the N-terminal amino group at the amino acid building block is protected by a base-labile protecting group.
19. The method of any one of the preceding items, wherein the N-terminal amino group at the amino acid building block is protected by Fmoc.
20. The method of any one of the preceding items, wherein the polypeptide is a GLP-1 agonist.
21. The method of any one of the preceding items, wherein the polypeptide is selected from GLP-1, analogs and derivatives thereof, exendin-3, analogs and derivatives thereof, and exendin-4, analogs and derivatives thereof.
22. The method of any one of the items 1 to 21, wherein the polypeptide is selected from exendin-4 and lixisenatide.
23. The method of any one of the items 1 to 22, wherein the polypeptide is lixisenatide.
24. The method of any one of the items 1 to 21, wherein the polypeptide is selected from albiglutide, dulaglutide and semaglutide.
25. The method of in item 1, wherein the polypeptide is lixisenatide, or exendin-4, wherein after coupling of the amino acid building block Arg(20), Glu (17), Gln(13), Leu(10) or/and Gly(4), step (b) is performed for about 10 min with a capping reagent comprising 2% v/v acetic anhydride and 1% v/v diisopropylethylamine.
26. Composition, characterized in that it comprises 0.5-5% v/v of acetic anhydride and 0.2-2% v/v of diisopropylethylamine in DMF.
27. The composition of item 26, comprising 1% v/v of diisopropylethylamine and 2% v/v of acetic anhydride.
28. Use of the composition of item 26 or 27 for acetylation of an unprotected amino group in polypeptide synthesis.
29. Use of the composition of item 28, wherein the polypeptide is lixisenatide.

The invention claimed is:

1. A method for the solid-phase synthesis of lixisenatide SEQ ID NO:1), the method comprising coupling cycles of amino acid building blocks of lixisenatide to an amino acid chain,
   wherein said amino acid building blocks comprise an unprotected C-terminal carboxyl group and a protected N-terminal amino group comprising an Fmoc protecting group,
   wherein said amino acid chain comprises an unprotected N-terminal amino group, and
   wherein at least one coupling cycle comprises the steps:
   (a) coupling the amino acid building block C-terminally at the unprotected N-terminal amino group of the amino acid chain, so that an amide bond is formed between the amino acid chain and the amino acid building block,
   (b) contacting the product obtained in step (a) with a capping reagent comprising a capping compound, wherein the capping compound binds to an unprotected N-terminal amino group of the amino acid chain to which no building block has been coupled in step (a), and
   (c) de-protecting the N-terminal amino group of the amino acid building block,
   wherein the method comprises sufficient coupling cycles to produce lixisenatide (SEQ ID NO:1), and
   wherein step (b) is performed after coupling of the amino acid building block at positions Arg(20), Glu(17), Gln (13, Leu(10) or Gly(4) of the lixisenatide sequence.

2. The method of claim 1, wherein the capping compound is selected from the group consisting of acetic anhydride (CAS 108-24-7), homologues of acetic anhydride, benzoyl chloride (CAS 98-88-4), N-(benzyloxycarbonyloxy)succinimide (CAS 13139-17-8), benzyl chloroformate (CAS 501-53-1), esters of chloroformic acid, 1-acetylimidazole (CAS 2466-76-4), di-tert-butyl dicarbonate (CAS 24424-99-5) and N-(tert-butoxycarbonyloxy)succinimide (CAS 13139-12-3).

3. The method of claim 1, wherein the capping reagent comprises 0.5-5% v/v of acetic anhydride.

4. The method of claim 1, wherein the capping reagent comprises 0.2-2% v/v of diisopropylethylamine (DIPEA).

5. The method of claim 1, wherein the capping reagent comprises a solvent that comprises N,N-dimethylformamide (DMF).

6. The method of claim 1, wherein the step (b) is performed at a temperature of 15-25° C.

7. The method of claim 1, wherein the step (b) is performed for 5 to 15 min.

8. The method of claim 1, wherein the amino acid building block is a single amino acid selected from ARg, Glu, Gln, Leu, and Gly.

9. The method of claim 3, where the capping reagent comprises 1-3% v/v of acetic anhydride.

10. The method of claim 3, where the capping reagent comprises 2% v/v of acetic anhydride.

11. The method of claim 4, where the capping reagent comprises 0.5-2% v/v of diisopropylethylamine (DIPEA).

12. The method of claim 4, where the capping reagent comprises 1% v/v of diisopropylethylamine (DIPEA).

13. The method of claim 1, further comprising the step of cleaving lixisenatide polypeptide linked to the solid phase after synthesis of the lixisenatide amino acid chain is completed.

14. A method for the solid-phase synthesis of lixisenatide, the method comprising coupling cycles of amino acid building blocks to an amino acid chain,
wherein said amino acid building blocks comprise an unprotected C-terminal carboxyl group and a protected N-terminal amino group comprising an Fmoc protecting group,
wherein said amino acid chain comprises an unprotected N-terminal amino group,
wherein at least one coupling cycle comprises the steps:
(a) coupling the amino acid building block C-terminally at the unprotected N-terminal amino group of the amino acid chain, so that an amide bond is formed between the amino acid chain and the amino acid building block,
(b) contacting the product obtained in step (a) with a capping reagent comprising a capping compound, wherein the capping compound binds to an unprotected N-terminal amino group of the amino acid chain to which no building block has been coupled in step (a), and
(c) de-protecting the N-terminal amino group of the amino acid building block, and
wherein the capping reagent comprises 0.5-5% v/v of acetic anhydride and 0.2-2% of diisopropylethylamine (DIPEA), and
wherein step (b) is performed after coupling of the amino acid building block at positions Arg(20), Glu(17), Gln (13, Leu(10) or Gly(4) of the lixisenatide sequence.

15. The method of claim 14, wherein the capping reagent comprises 1-3% v/v of diisopropylethylamine (DIPEA) and 2% v/v of acetic anhydride.

16. The method of claim 14, wherein the capping reagent comprises N,N-dimethylformamide (DMF).

17. The method of claim 14, wherein the step (b) is performed at a temperature of 15-25° C.

18. The method of claim 14, wherein the step (b) is performed for 5 to 15 min.

19. The method of claim 14, where the capping reagent comprises 2% v/v of acetic anhydride and 1% v/v of diisopropylethylamine (DIPEA).

20. The method of claim 14, further comprising the step of cleaving lixisenatide polypeptide linked to the solid phase after synthesis of the lixisenatide amino acid chain is completed.

21. The method of claim 14, wherein the amino acid building block is a single amino acid selected from Arg, Glu, Gln, Leu and Gly.

\* \* \* \* \*

SEQUENCE LISTING

```
<160> NUMBER OF SEQ ID NOS: 4

<210> SEQ ID NO 1
<211> LENGTH: 44
<212> TYPE: PRT
<213> ORGANISM: Artificial Sequence
<220> FEATURE:
<223> OTHER INFORMATION: lixisenatide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Heloderma suspectum
<220> FEATURE:
<223> OTHER INFORMATION: exendin-4
```

```
<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Heloderma horridum
<220> FEATURE:
<223> OTHER INFORMATION: exendin-3

<400> SEQUENCE: 3

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 30
<212> TYPE: PRT
<213> ORGANISM: human
<220> FEATURE:
<223> OTHER INFORMATION: GLP-1(7-36)

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```